United States Patent
Fritsch et al.

(10) Patent No.: US 8,434,183 B2
(45) Date of Patent: May 7, 2013

(54) BRUSH SECTION FOR AN ELECTRIC TOOTHBRUSH

(75) Inventors: Thomas Fritsch, Eppstein (DE); Ulrich Störkel, Bad Nauheim (DE)

(73) Assignee: Braun GmbH, Kronberg (DE)

( * ) Notice: Subject to any disclaimer, the term of this patent is extended or adjusted under 35 U.S.C. 154(b) by 315 days.

(21) Appl. No.: 12/855,945

(22) Filed: Aug. 13, 2010

(65) Prior Publication Data

US 2012/0036655 A1   Feb. 16, 2012

(51) Int. Cl.
*A61C 17/22* (2006.01)
*A61C 17/32* (2006.01)
*A61C 17/34* (2006.01)
*A46B 9/04* (2006.01)
*A46B 7/06* (2006.01)
*A47L 21/02* (2006.01)
*A47L 23/02* (2006.01)

(52) U.S. Cl.
USPC .............. 15/22.1; 15/167.1; 15/22.2; 15/201; 15/167.2; 15/28

(58) Field of Classification Search ............. 15/22.1, 15/22.2, 32, 33, 167.1, 167.2, 201, 207.2, 15/28; 132/308–311
See application file for complete search history.

(56) References Cited

U.S. PATENT DOCUMENTS

| | | | |
|---|---|---|---|
| 2,882,544 A * | 4/1959 | Hadidian | 15/167.1 |
| 4,633,542 A * | 1/1987 | Taravel | 15/167.1 |
| 5,077,855 A | 1/1992 | Ambasz | |
| 5,088,145 A * | 2/1992 | Whitefield | 15/22.1 |
| 5,398,366 A * | 3/1995 | Bradley | 15/167.1 |
| 5,504,958 A | 4/1996 | Herzog | |
| 5,850,655 A * | 12/1998 | Gocking et al. | 15/28 |
| 5,876,207 A * | 3/1999 | Sundius et al. | 433/216 |
| 6,308,358 B2 * | 10/2001 | Gruber et al. | 15/22.1 |
| 6,601,257 B1 * | 8/2003 | Felix-Flender et al. | 15/160 |
| 6,725,490 B2 * | 4/2004 | Blaustein et al. | 15/22.2 |
| 6,785,929 B2 * | 9/2004 | Fritsch et al. | 15/167.1 |
| 6,928,685 B1 * | 8/2005 | Blaustein et al. | 15/22.1 |
| 7,024,718 B2 * | 4/2006 | Chu | 15/22.2 |
| 7,117,555 B2 * | 10/2006 | Fattori et al. | 15/22.2 |
| 7,162,764 B2 * | 1/2007 | Drossler et al. | 15/22.1 |
| 7,392,562 B2 * | 7/2008 | Boland et al. | 15/28 |
| 7,520,016 B2 * | 4/2009 | Kressner | 15/22.1 |
| 7,614,111 B2 * | 11/2009 | Moskovich et al. | 15/167.1 |
| 7,640,614 B2 * | 1/2010 | Brown et al. | 15/22.1 |
| 7,841,041 B2 * | 11/2010 | Moskovich et al. | 15/167.1 |
| 7,861,350 B2 * | 1/2011 | Brown et al. | 15/22.1 |

(Continued)

FOREIGN PATENT DOCUMENTS

DE     35 44 256 A1    6/1987
WO    WO 2008/040401   4/2008

*Primary Examiner* — Vanitha Elgart
(74) *Attorney, Agent, or Firm* — John P. Colbert

(57) ABSTRACT

A brush section for use with an electric toothbrush includes a movable contact element holder and a fixed contact element holder. The movable contact element holder is driven to move relative to the fixed contact element holder by an electric drive in a handle section which is coupled to the movable contact element holder. The risk of oral mucosa being pinched by the movement is minimized by any one of several methods, such as for example reducing the width of the gap between the two holders, adding a cover member, reducing the movement of the movable contact element holder, and the like. In addition, a low profile brush section is provided.

11 Claims, 19 Drawing Sheets

U.S. PATENT DOCUMENTS

| | | | | |
|---|---|---|---|---|
| 7,917,984 | B2* | 4/2011 | Blaustein et al. | 15/22.1 |
| 7,962,988 | B2* | 6/2011 | Sorrentino | 15/22.1 |
| 8,032,964 | B2* | 10/2011 | Farrell et al. | 15/22.1 |
| 8,151,397 | B2* | 4/2012 | Moskovich et al. | 15/201 |
| 8,239,995 | B2* | 8/2012 | Chenvainu et al. | 15/167.1 |
| 2002/0138926 | A1* | 10/2002 | Brown et al. | 15/22.1 |
| 2003/0154567 | A1* | 8/2003 | Drossler et al. | 15/22.1 |
| 2003/0163881 | A1* | 9/2003 | Driesen et al. | 15/22.1 |
| 2004/0083566 | A1* | 5/2004 | Blaustein et al. | 15/22.1 |
| 2004/0088806 | A1* | 5/2004 | DePuydt et al. | 15/22.1 |
| 2005/0000043 | A1 | 1/2005 | Chan et al. | |
| 2005/0091771 | A1* | 5/2005 | Blaustein et al. | 15/22.1 |
| 2006/0010623 | A1* | 1/2006 | Crossman et al. | 15/22.1 |
| 2006/0075588 | A1* | 4/2006 | Amador | 15/167.1 |
| 2006/0156495 | A1* | 7/2006 | Chan et al. | 15/22.1 |
| 2006/0200922 | A1* | 9/2006 | Hohlbein | 15/22.1 |
| 2006/0272112 | A9* | 12/2006 | Braun et al. | 15/22.1 |
| 2007/0006403 | A1* | 1/2007 | DePuydt et al. | 15/22.1 |
| 2007/0033757 | A1* | 2/2007 | Storkel et al. | 15/167.1 |
| 2007/0294847 | A1* | 12/2007 | Wang | 15/22.2 |
| 2008/0030759 | A1 | 2/2008 | Farrell et al. | |
| 2008/0086827 | A1* | 4/2008 | Waguespack et al. | 15/105 |
| 2008/0313830 | A1* | 12/2008 | Gatzemeyer et al. | 15/22.1 |
| 2009/0183324 | A1 | 7/2009 | Fischer et al. | |
| 2009/0211043 | A1* | 8/2009 | Kressner | 15/22.1 |
| 2010/0162499 | A1* | 7/2010 | Braun et al. | 15/22.1 |
| 2010/0306943 | A1* | 12/2010 | Storkel et al. | 15/167.1 |
| 2010/0313373 | A1* | 12/2010 | Stief et al. | 15/167.1 |
| 2010/0325823 | A1* | 12/2010 | Kressner | 15/22.1 |
| 2010/0330538 | A1* | 12/2010 | Salazar et al. | 433/216 |
| 2011/0005014 | A1* | 1/2011 | Kressner | 15/22.1 |
| 2011/0072599 | A1* | 3/2011 | Brown et al. | 15/22.1 |
| 2011/0138561 | A1* | 6/2011 | Stoerkel et al. | 15/167.1 |
| 2011/0179594 | A1* | 7/2011 | Zini | 15/167.1 |
| 2011/0283468 | A1* | 11/2011 | Sorrentino | 15/4 |
| 2011/0289702 | A1* | 12/2011 | Lee | 15/22.1 |
| 2012/0000023 | A1* | 1/2012 | Farrell et al. | 15/22.4 |
| 2012/0036656 | A1* | 2/2012 | Fritsch et al. | 15/22.1 |
| 2012/0042459 | A1* | 2/2012 | Khudoley | 15/22.2 |
| 2012/0159722 | A1* | 6/2012 | Fritsch et al. | 15/22.1 |

* cited by examiner

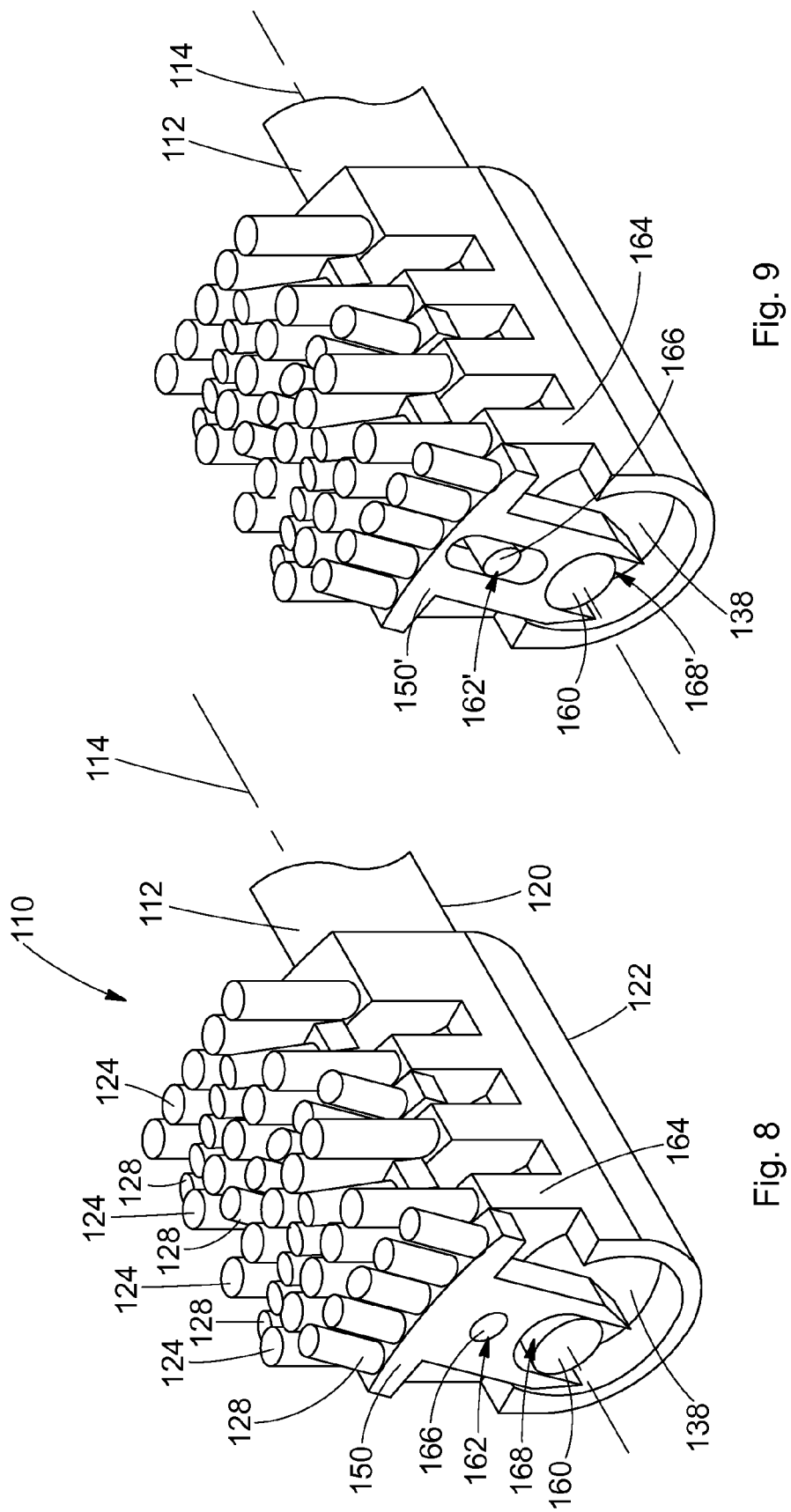

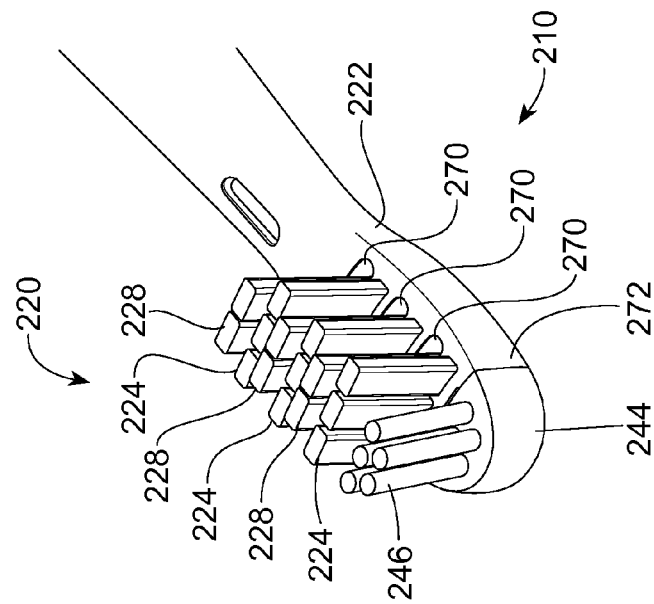
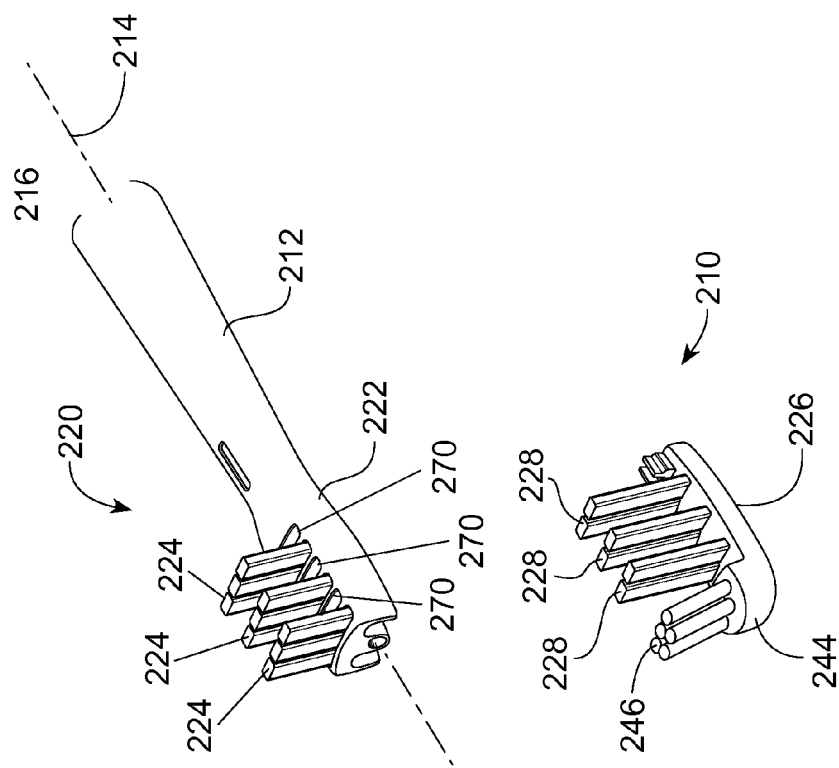

BRUSH SECTION FOR AN ELECTRIC TOOTHBRUSH

FIELD OF THE INVENTION

This application relates to electric toothbrushes and in particular to a brush section for an electric toothbrush.

BACKGROUND OF THE INVENTION

An electric toothbrush may incorporate a brush section that couples to a handle section. A drive shaft may extend from the handle section with the drive shaft being coupled to an electric drive disposed within an interior of the handle section. The electric drive may impart a rotary, oscillating or combined rotary oscillating motion to the drive shaft so that the drive shaft is movable in a rotary or oscillating manner. The brush section can couple and secure to the handle section with the drive shaft coupling to a coupling element of the brush section, e.g., a shaft or drive pin. The motion of the drive shaft can be imparted upon the coupling element to provide a desired cleaning action to a brush head portion of the brush section.

One such toothbrush brush section is disclosed in U.S. Patent Application Publication No. 2008/0307591 to inventors Farrell et al. As more fully described in that prior application, it concerns electric toothbrush designs which are particularly suitable for use in conjunction with a traditional manual brushing action. The present application sets forth several improvements to the designs of Farrell et al., and other previously known toothbrush designs. More specifically, the present application sets forth a brush head construction which minimizes the likelihood of pinching mucosa within a user's mouth, by minimizing gaps between brush sections which move relative to one another. As used herein, "mucosa" is broadly defined to include all soft tissues within a person's mouth, such as the interior cheek surfaces, the gum tissue, the lip tissue, and the tongue. A low profile brush section is also provided herein.

SUMMARY OF THE INVENTION

In one embodiment, a cleaning section for an electrical toothbrush having a motor includes a head portion and a movable contact element holder having a range of motion relative to the head portion, movable contact elements supported within the movable contact element holder; and a gap disposed between the head portion and the movable contact element holder. The movable contact element holder is structured to receive a drive motion from the motor via a drive mechanism comprising a drive shaft having a longitudinal axis, the drive shaft being structured to translate a motion generated by the motor to the movable contact element holder. The width of the gap remains between about 0.1 millimeter and about 0.6 millimeter throughout a full range of motion of the movable contact element holder.

In another embodiment, a cleaning section for an electrical toothbrush having a motor, includes a head portion and a movable contact element holder having a range of motion relative to the head portion; and movable contact elements supported within the movable contact element holder. The movable contact element holder is structured to receive a drive motion from the motor via a drive mechanism comprising a drive shaft having a longitudinal axis, the drive shaft being structured to translate a motion generated by the motor to the movable contact element holder. And, a portion of the movable contact element holder is exposed to an exterior of the cleaning section.

In yet another embodiment, a cleaning section for an electrical toothbrush having a motor includes a head portion and a movable contact element holder having a range of motion relative to the head portion; and movable contact elements supported within the movable contact element holder, such that the movable contact elements extend upwardly through apertures disposed in the head portion. The movable contact element holder is structured to receive a drive motion from the motor via a drive mechanism comprising a drive shaft having a longitudinal axis, the drive shaft being structured to translate a motion generated by the motor to the movable contact element holder. And, as the movable contact element holder moves through the range of motion, at least a lower fifty percent of the height of the movable contact elements remains within vertical envelopes defined by the apertures.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

FIG. 8 is a schematic partial perspective view of another brush head portion arrangement.

FIG. 9 is a schematic partial perspective view of a further alternative brush head portion arrangement.

FIG. 13A is an exploded perspective view of another brush section.

FIG. 13B is a perspective view of the brush section illustrated in FIG. 13A, in an assembled condition.

DETAILED DESCRIPTION OF THE INVENTION

Figure 1:
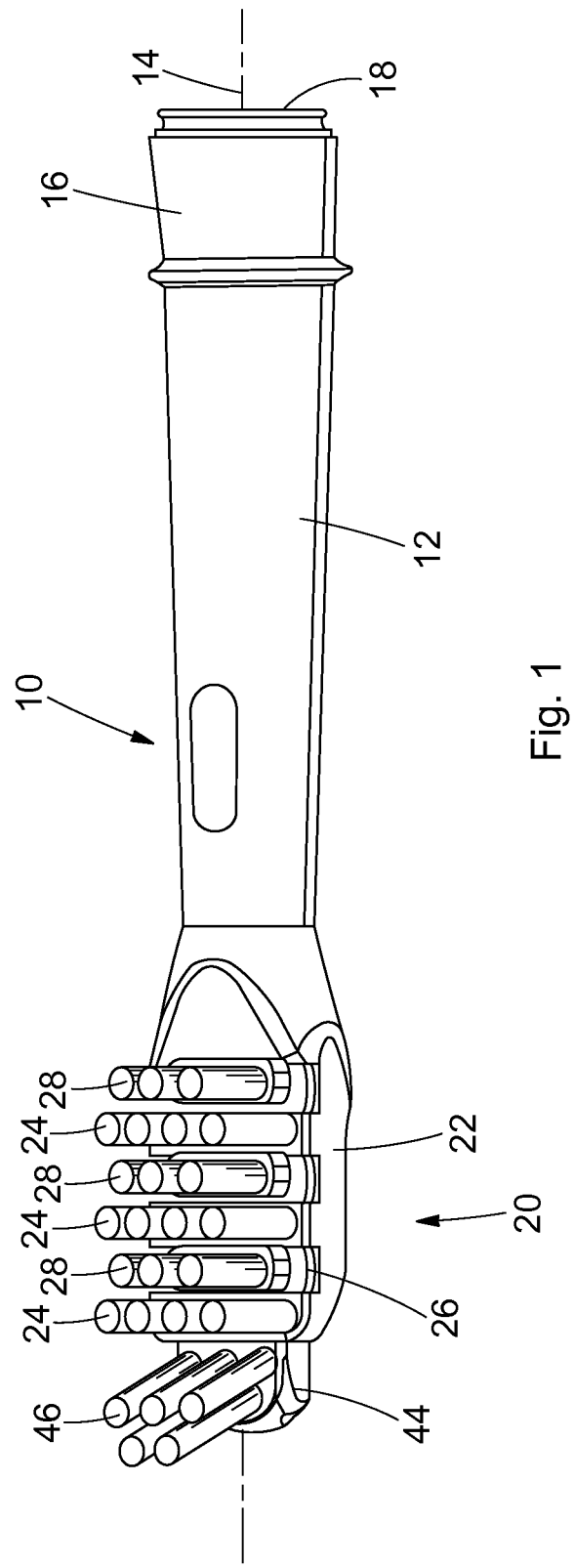
FIG. 1 is a schematic top view of a brush section.

A brush section for use with an electric toothbrush includes a brush head portion which may have a generally rectangular shape, although oblong, elliptical, or any suitable shape may be employed. Generally, the brush head portion may have a length-to-width aspect ratio greater than 1, although such an arrangement is not required. The brush head portion is secured to a tube member of the brush section that may be configured to couple to a handle section. The handle section may include an electric drive including a drive shaft, and the drive shaft may couple to the brush head via a coupling or drive pin member positioned within the tube member. In some embodiments, the electric drive may impart a rotary, oscillating, rotary-oscillating or other suitable drive motion to the drive shaft that is, in turn, imparted upon the brush head and bristle members thereof by virtue of the coupling member.

The brush head may incorporate a first plurality of cleaning bristles that are static, i.e., fixed relative to the brush head and a second plurality of cleaning bristles that are movable in a cleaning motion relative to the first plurality of bristles. For example, the second plurality of cleaning bristles may include a bristle support structure or bristle holder that is supported within the brush head to have at least one direction of freedom to move relative to the brush head and the first plurality of bristles. In one embodiment, the bristle support structure may be free to pivot about a first axis relative to the brush head. The coupling member couples the bristle support structure to the electric drive for driving the bristle support structure causing the second plurality of bristles to have the desired cleaning motion. The bristle support structure may comprise a plurality of separate bristle support structures such that each structure may move independently with respect to each other separate bristle support structure. Furthermore, the cleaning motion may include an eccentric motion or translational motion in combination with a rotary, oscillating or other suitable cleaning motion.

It will be understood and appreciated that while various aspects, features and advantages of the invention are described in connection with particular embodiments, the herein described aspects, features and advantages may be implemented in any of the embodiments, and as such, the features and structures of the various embodiments may be mixed and matched yielding a virtually limitless number of combinations. One of skill in the art will furthermore appreciate that the herein described aspects, features and advantages of the invention may be combined with structures and devices known to or later discovered by the skilled artisan.

The herein described embodiments of brush sections are suited to operate in conjunction with an electric toothbrush, such as for example an electric toothbrush of the type having a handle section including an electric drive and a drive shaft having a longitudinal axis. The electric drive imparts a motion to the drive shaft. It may, for example, impart a rotary, oscillating, or rotary and oscillating motion to the drive shaft. The motion of the drive shaft is coupled to the brush section to impart a desired motion to a brush head portion of the brush section such that the brush head portion, or any component thereof, is caused to have a desired cleaning motion. Many different kinds of cleaning motions, including rotary, oscillating, vertical and/or horizontal sweeping and the like, may be used. Generally, as used herein, cleaning motion describes any desired or effective movement of the bristles relative to the brush head to affect cleaning. Handle sections, as described above, are well known to the skilled artisan. In addition, the brush sections may be configured for use with such existing handle sections or may be configured with new handle section types, as the case may be.

Figure 2:
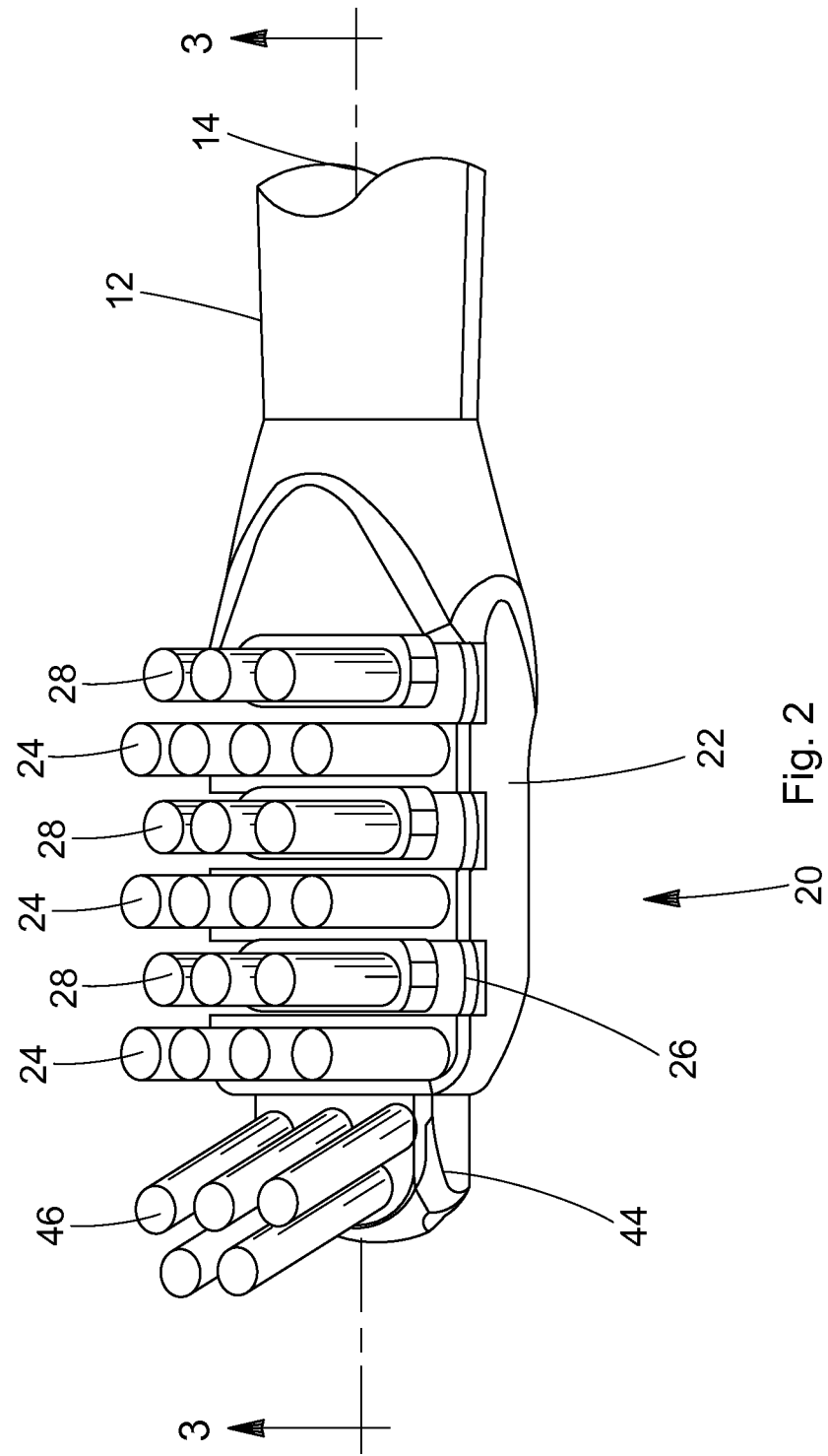
FIG. 2 is a schematic partial top view of a brush head portion of the brush section illustrated in FIG. 1.
Figure 3:
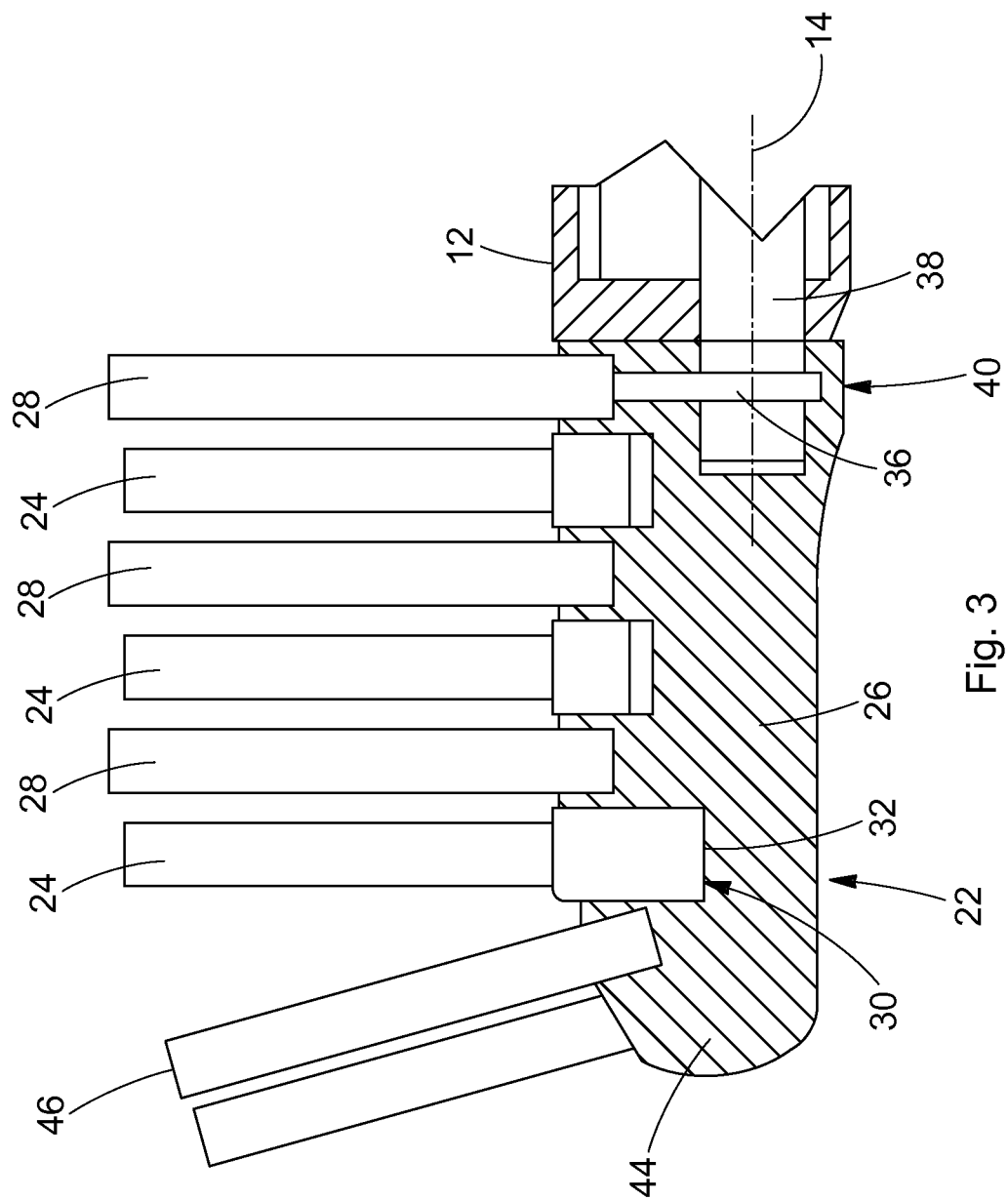
FIG. 3 is a schematic cross-section view of the brush head portion illustrated in FIG. 2.

FIGS. 1-3 illustrate a brush section 10 which may be push-fitted onto a toothbrush handle section and coupled to the drive shaft of the handle section, such as for example a handle section described above. The brush section includes a mounting tube 12 extending along an axis 14. The axis 14 is a longitudinal axis of the cleaning section and may coincide with a longitudinal section of the drive shaft 38 (FIG. 3). At a first end 16 (FIG. 1), the mounting tube 12 may include a profile ring 18 having an inside contour complementary with an outside contour of the handle section. In this manner, the brush section 10 can be push-fitted onto the handle section in a manner preventing relative rotation of the brush section with respect to the handle section. A tab/slot, key/spline or other similar structure may be included in the corresponding contour surfaces to facilitate alignment of the brush section with the handle section and to further prevent relative rotation between the two.

At a second end 20 the brush section 10 includes a brush head portion 22. In some embodiments, the brush head portion 22 supports a first plurality of contact elements 24 that are mounted to the head portion 22 so as to be fixed, i.e., they are static relative to the head portion 22. Any suitable method of mounting the first plurality of contact elements 24 to the head portion 22 may be used. For example, where the contact elements 24 comprise a plurality of bristles, methods, such as hot tufting, gluing, stapling, and the like, may be utilized. As another example, where the contact elements 24 comprise a plurality of elastomeric elements, methods such as gluing, snap-fitting, welding, molding, etc. may be utilized.

Supported within the head portion 22 is a movable contact element support or movable contact element holder 26 supporting a second plurality of contact elements 28. The second plurality of contact elements 28 may be mounted to the movable contact element holder 26 using any suitable method, as described above with regard to the first plurality of contact elements 24. The movable contact element holder 26 may be supported within the head portion 22 such that it is able to rotate about the longitudinal axis 14 responsive to a suitable driving input from the handle section.

The first plurality of contact elements 24 may have a first height and the second plurality of contact elements 28 may have a second height, different than the first height. Additionally, the ends of the first and second pluralities of contact elements 24 and 28 may have contoured, rounded or otherwise shaped ends. Among the first plurality of contact elements 24 and the second plurality of contact elements 28, contact elements or tufts of bristles (in embodiments where the contact elements comprise a plurality of bristles) at different locations of the head portion 22, e.g. front to back and/or center to edge, may also have different heights and different bristle end contours.

The first plurality of contact elements 24 may be arranged in rows transverse relative to the axis 14. Similarly, the second plurality of contact elements 28 may be arranged in rows transverse relative to the axis 14. In some embodiments, the transverse rows may alternate between rows of first plurality of contact elements 24 and rows of second plurality of contact elements 28. In some embodiments, multiple rows of the first plurality of contact elements may be separated by a row or multiple rows of the second plurality of contact elements 28 and vice versa or the rows may be interleaved or arranged in virtually any manner.

As shown in FIG. 3, in some embodiments, the head portion 22 may include a first bearing surface 30 that engages a recess, notch, slot or other suitable formation 32 formed in the movable contact element holder 26. As shown, in some embodiments, the recess, notch, slot, or other suitable formation 32 may be disposed between the second plurality of contact elements 28 and a third plurality of contact elements 46.

A drive shaft 38 may engage the movable contact element holder 26 such that movement of the drive shaft 38 can be transferred to the movable contact element holder 26. The drive shaft 38 may be supported within the mounting tube 12 at a rearward end 40 of the head portion 22. The drive shaft 38 may be joined to the contact element holder 26 via any suitable means. For example, as shown, the drive shaft 38 may be joined to the movable contact element holder 26 via a drive pin 36. As yet other examples, the drive shaft 38 may be joined to the movable contact element holder 26 adhesively, chemically, mechanically, electrically, e.g. magnetic clutch, or any combination thereof. In some embodiments, the drive pin 36 may be inserted into the movable contact element holder 26 and/or the drive shaft 38 via corresponding apertures in the movable contact holder 26 and/or drive shaft 38.

Figure 4:
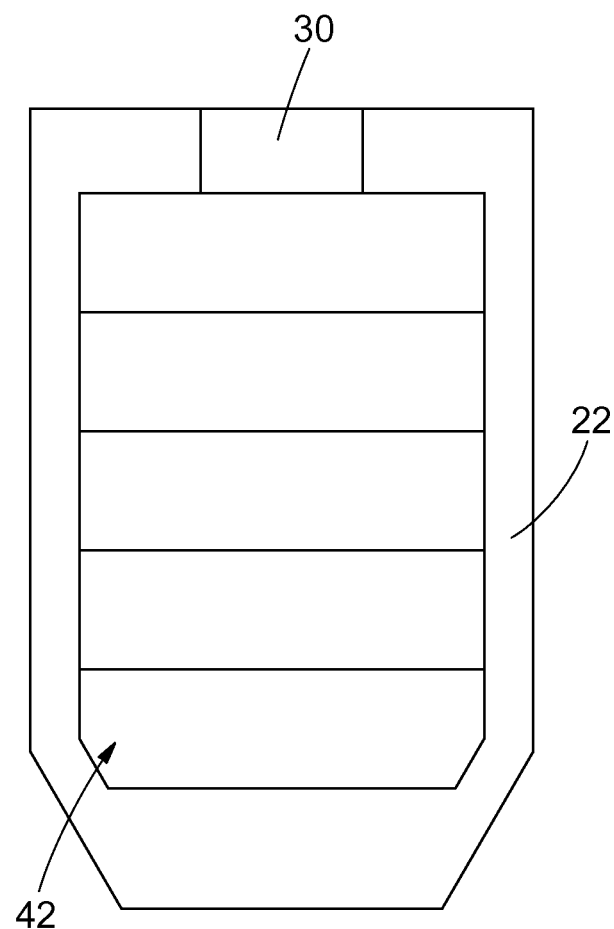
FIG. 4 is a schematic top view of the brush head portion of FIG. 2 with the cleaning element fields removed for visual facilitation.

As shown in FIG. 4, the movable contact element holder 26 (shown in FIGS. 1-3) may be snap-fitted into the head portion 22 via an opening 42. The opening 42 may then be closed with a snap-in-place housing member (not depicted).

In the embodiment shown in FIGS. 1-3, the movable contact element holder 26 may include an extension portion 44 supporting the third plurality of contact elements 46. The extension portion 44 may be supported to permit at least one freedom of motion relative to the head portion 22. For example, the extension portion 44 may be supported to rotate relative to the head portion 22. In this manner, the third plurality of contact elements 46 may move in a cleaning motion relative to the first plurality of contact elements 24 and/or the second plurality of contact elements 28. For example, the extension portion 44 may couple to the movable bristle holder 26 such that the third plurality of contact elements 46 moves in a similar manner as the second plurality of contact elements 28.

In other embodiments, the brush head portion 22 comprises the extension portion 44 and the third plurality of contact elements 46. In such embodiments, the third plurality of contact elements 46 may be stationary with respect to the brush head portion 22.

Referring back to FIG. 3, in some embodiments, the coupling between the extension portion 44 and the movable contact element holder 26 may be direct such that the extension portion 44 moves with the movable contact element holder 26. However, in some embodiments, the extension portion 44 may couple to the drive shaft 38, directly, via a cam arrangement, a linkage or otherwise, and/or to the movable contact element holder 26 or otherwise such that the extension portion 44 has a cleaning motion that is separate from a cleaning motion of the movable contact element holder 26 and the second plurality of contact elements 28.

In the embodiment shown in FIGS. 1-3, the movable contact element holder 26 may oscillate about the axis 14 thereby causing the second plurality of contact elements 28 and/or the third plurality of contact elements 46 to similarly oscillate about the axis 14. The movement of the movable contact element holder 26 may cause the second plurality of contact elements 28 and/or the third plurality of contact elements 46 to oscillate back and forth angularly to provide a cleaning action substantially similar to an up-down manual brushing action.

The amount of angular movement as well as the speed exhibited by the movable contact element holder 26 and the second plurality of contact elements 28 and/or the third plurality of contact elements 46 can impact the efficacy of the cleaning action. Generally, an oscillation angle within the range of 40-60 degrees is considered beneficial. For example, the movable contact element holder 26 may move through an angle of about 44 degrees, i.e., +/−22 degrees relative to the head portion 22, in some embodiments. Another example includes a 55 degrees angle. However, any suitable angle may be utilized. For example, other angles greater than 55 degrees or less than 44 degrees may be used.

In some embodiments, the movable contact element holder 26 can move through an angle of from about 10 degrees to about 90 degrees, or any individual number within the range. In some embodiments, the movable contact element holder 26 can move through an angle greater than about 10 degrees, greater than about 12 degrees, greater than about 15 degrees, greater than about 18 degrees, greater than about 20 degrees, greater than about 22.5 degrees, greater than about 25 degrees, greater than about 30 degrees, greater than about 35 degrees, greater than about 40 degrees, greater than about 45 degrees, greater than about 50 degrees, greater than about 55 degrees, greater than about 60 degrees, greater than about 65 degrees, greater than about 70 degrees, greater than about 75 degrees, greater than about 80 degrees, greater than about 85 degrees, and/or less than about 90 degrees, less than about 85 degrees, less than about 80 degrees, less than about 75 degrees, less than about 70 degrees, less than about 65 degrees, less than about 60 degrees, less than about 55 degrees, less than about 50 degrees, less than about 45 degrees, less than about 40 degrees, less than about 35 degrees, less than about 30 degrees, less than about 25 degrees, less than about 22.45 degrees, less than about 20 degrees, less than about 18 degrees, less than about 15 degrees, less than about 12 degrees, or less than about 10 degrees.

As stated above, the speed at which the movable contact element holder 26 and the second plurality of contact elements 28 and/or the third plurality of contact elements 46 move through their angular movement may also impact the efficacy of the cleaning action. For example, a speed of about 75 Hz may provide adequate cleaning where the movable contact element holder 26 moves through an angle of about 44 degrees. In general, where the movable contact element holder 26 moves through a smaller angle, the speed at which the movable contact element holder 26 moves through the angle may increase in order to maintain cleaning efficacy.

The movable contact element holder 26 may move through its respective angle at a speed ranging from between about 30 Hz to about 130 Hz, or any individual number within the range. In some embodiments, the movable contact element holder 26 may move through its respective angle at a speed of greater than about 30 Hz, greater than about 40 Hz, greater than about 50 Hz, greater than about 60 Hz, greater than about 70 Hz, greater than about 80 Hz, greater than about 90 Hz, greater than about 100 Hz, greater than about 110 Hz, greater than about 120 Hz, and/or less than about 130 Hz, less than about 120 Hz, less than about 110 Hz, less than about 100 Hz, less than about 90 Hz, less than about 80 Hz, less than about 70 Hz, less than about 60 Hz, less than about 50 Hz, or less than about 40 Hz.

Advantageously, with the movement of the second plurality of contact elements 28 and/or the movement of the third plurality of contact elements 46, and a manually imparted cleaning movement of the overall head portion 22, the user may experience an enhanced and effective cleaning action. Furthermore, instead of the user's manual manipulation of the toothbrush incorporating the brush section 10 drawing away from, and degrading, the driven cleaning action, the two actions may combine to provide an enhanced cleaning affect. Also, in the event that the handle section becomes discharged and thus the electric drive becomes disabled, the brush section 10 may be easily used in the same manner as a manual toothbrush to affect cleaning.

In some embodiments, the brush section 10 may comprise a transponder, and the handle section may comprise a detector or a reading device as described in U.S. Patent Application Publication Nos. 2004/0255409 and 2003/0101526. The transponder can be configured to communicate information about the brush section 10 to the detector or reading device. The reading device or detector can be in signal communication with a controller which may be configured to control the speed of a motor and/or the angular motion of a shaft of the motor. The basic architecture of a controller, reading device, detector, and/or transponder is generally known.

The speed of the motor as well as the angle of oscillatory shaft displacement can be controlled in any suitable manner. For example, one means of modifying the speed of the motor is to increase or decrease the voltage to the motor. Typically, an increase in voltage will increase the speed of the motor while a decrease in voltage will decrease the speed of the motor. Such mechanisms for modifying the voltage delivered to motors are well known. As another example, the speed of the motor may be modified via a transmission system.

Figure 11A:
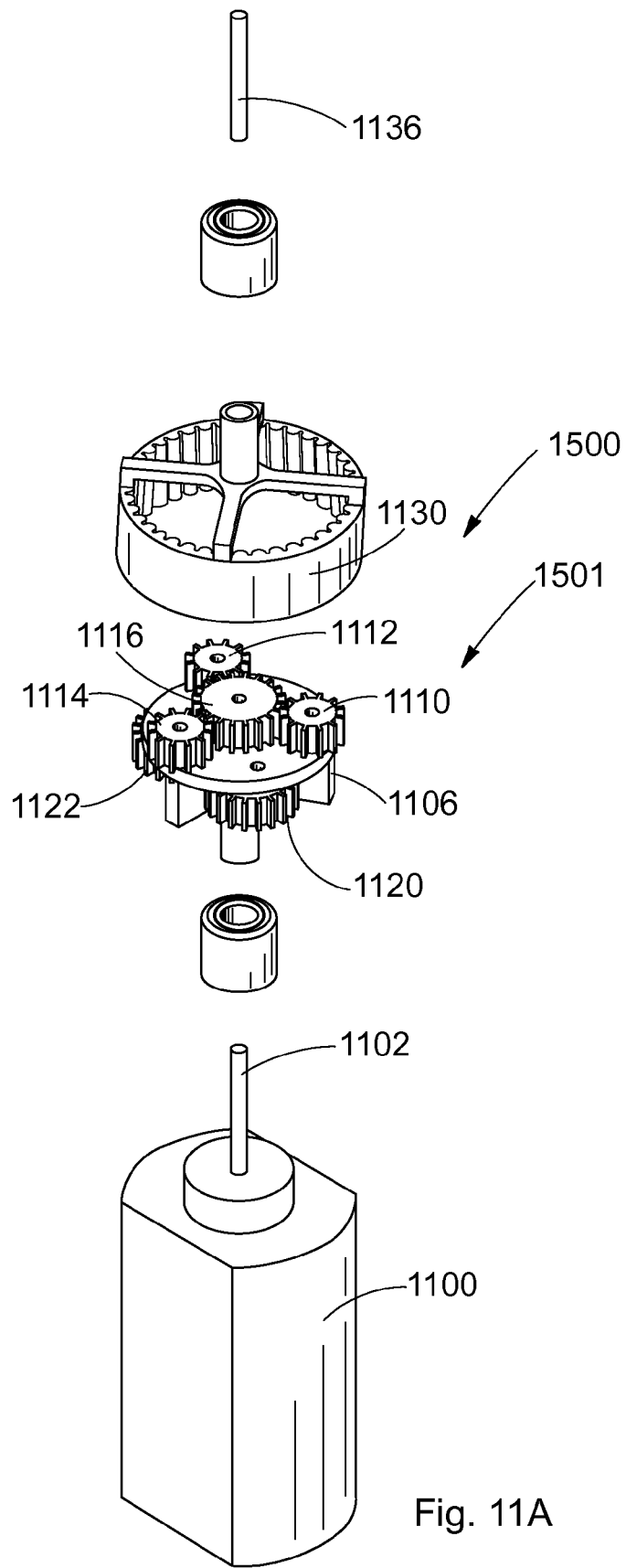
FIG. 11A is a schematic exploded view of a drive system suitable for use in the present invention.
Figure 11B:
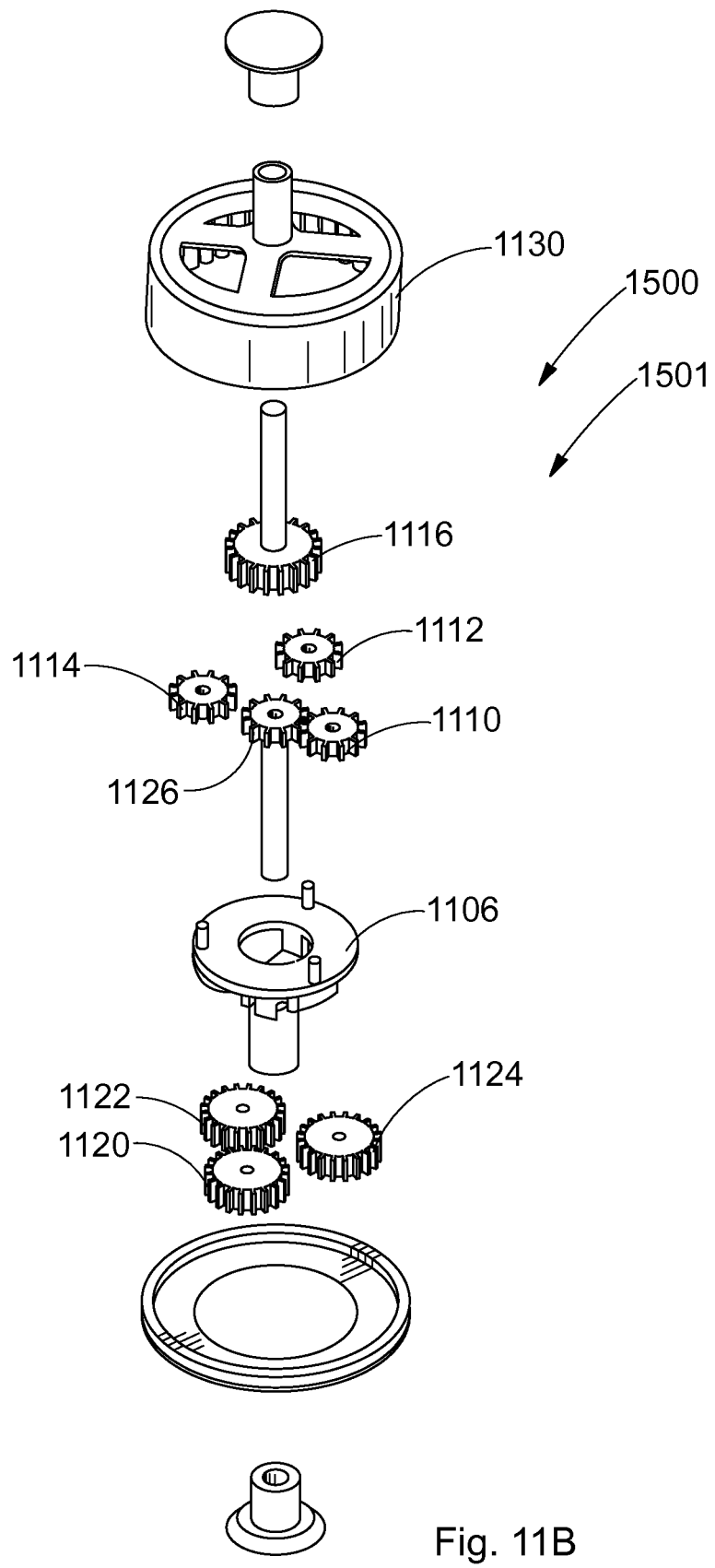
FIG. 11B is a schematic exploded view of the drive system of FIG. 11A.

FIGS. 11A and 11B illustrate one embodiment of a transmission system. A transmission system 1500 may comprise a drive system 1501. The drive system 1501 may comprise a motor 1100 having a shaft 1102. The shaft 1102 may be operatively connected to a first driver 1126 and/or a second driver 1116. In a first configuration, the teeth of the first driver 1126 may be intermeshed with teeth from a plurality of planetary gears 1120, 1122, and/or 1124. In a second configuration, the teeth of the second driver 1116 may be intermeshed with teeth from a plurality of planetary gears 1110, 1112, and/or 1114.

As shown, the first driver 1126 and/or the second driver 1116 as well as their respective planetary gears may be disposed on a gear carrier 1106. The planetary gears may be rotatably connected to the gear carrier 1106.

A ring gear 1130 may comprise complementary teeth to those of the planetary gears. As such, the teeth of the ring gear 1130 may intermesh with the teeth of the planetary gears. In some embodiments, an output shaft 1136 may be operatively connected to the ring gear 1130. In such embodiments, the ring gear 1130 may be driven at various speeds depending on the size of the driver gear and its respective planetary gears. For example, as shown, the first driver 1126 may have a smaller diameter than the second driver 1116. As such, the corresponding planetary gears, e.g. 1120, 1122, and/or 1124 may have larger diameters than the first driver 1126. So, in the first configuration, for a predetermined rotational speed of the motor shaft 1102, the ring gear 1130 may have a rotational speed which is less than the rotational speed of the motor shaft 1102. In contrast, in the second configuration, for a predetermined rotational speed of the motor shaft 1102, the ring gear 1130 may have a rotational speed which is greater than the rotational speed of the motor shaft 1102. In the second configuration, the second driver 1116 may have a diameter which is greater than the diameter of its respective planetary gears, e.g. 1110, 1112, and/or 1114. The selection of the first driver 1126 and/or the second driver 1116 may be created via a clutch system or any other suitable means.

In some embodiments, the first driver 1126 and/or the second driver 1116 may be operatively connected to the output shaft 1136. In such embodiments, the ring gear 1130 may be driven by the shaft 1102 while the gear carrier 1106 remains stationary. Alternatively, the gear carrier 1106 may be driven by the shaft 1102 while the ring gear 1130 remains stationary.

Figure 12A:
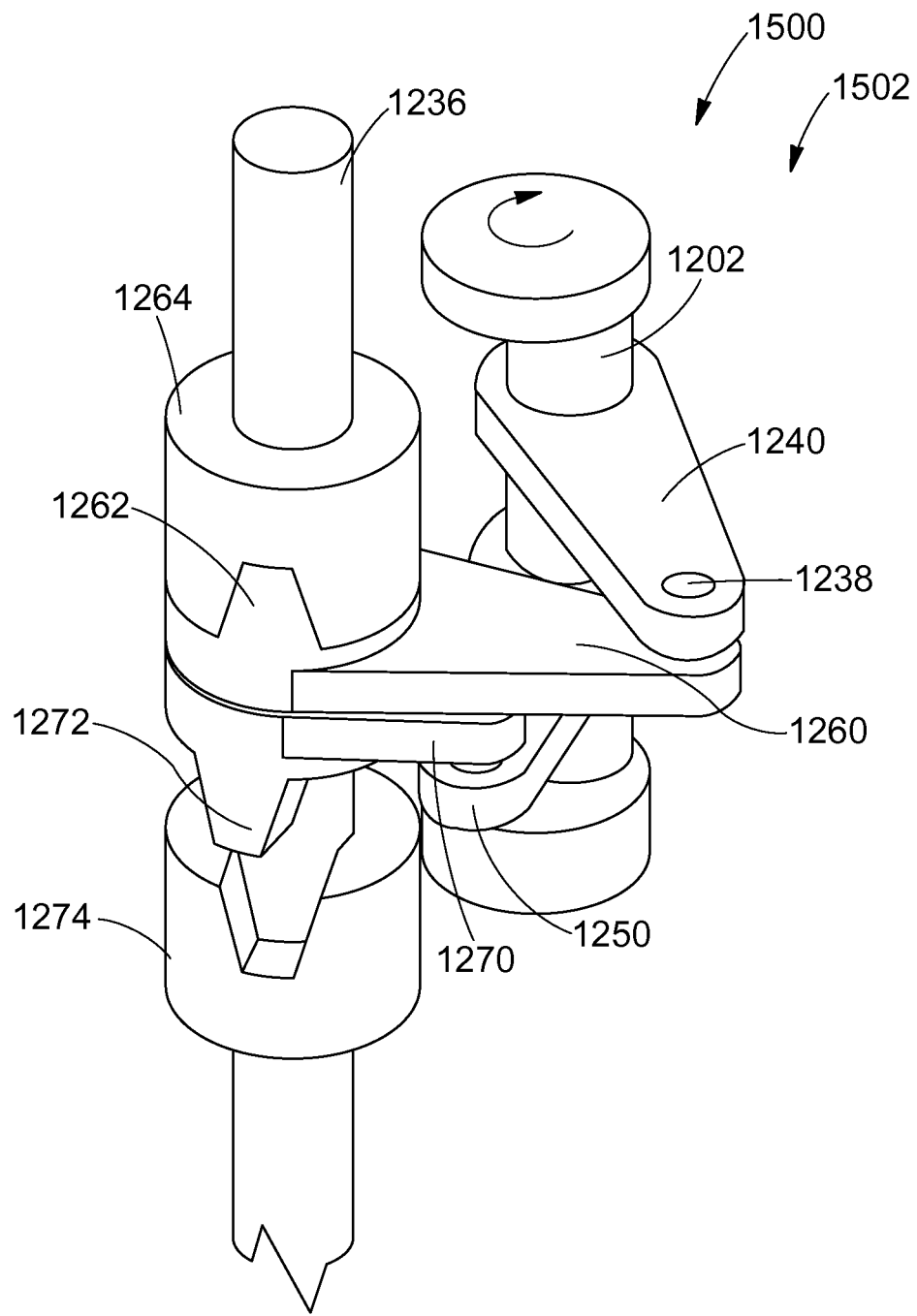
FIGS. 12A and 12B are schematic elevation views showing an output system suitable for use in the present invention.
Figure 12B:
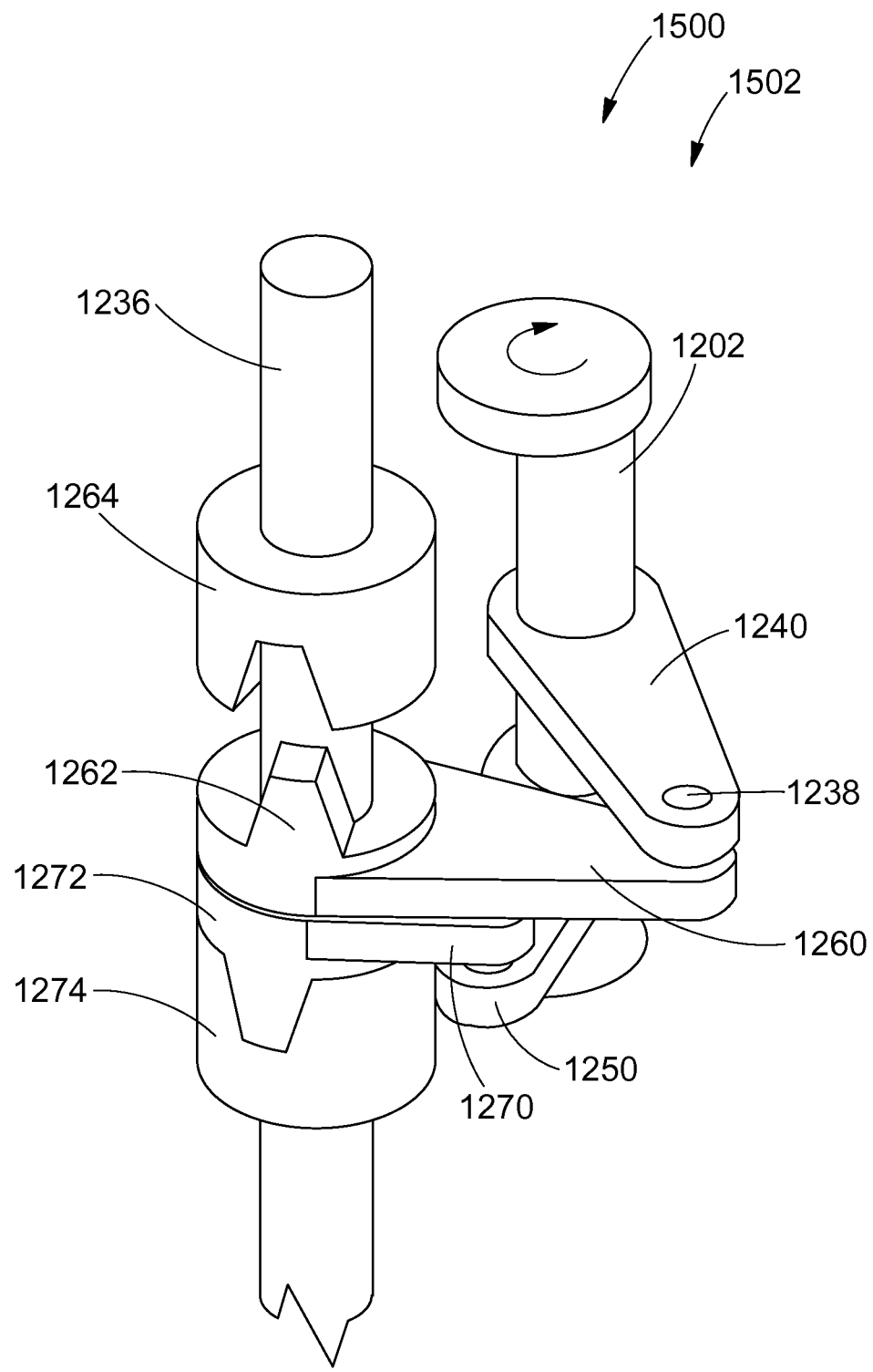

Additionally, as stated previously, the angle may be modified in any suitable manner. For example, as shown in FIGS. 12A and 12B, the transmission system 1500 may further comprise an output system 1502. Embodiments are contemplated where devices of the present invention include the drive system 1501 and/or the output system 1502.

As shown in FIGS. 12A and 12B, the output system 1502 may comprise a shaft 1202, a first driver linkage 1240, a first driven linkage 1260, a second driver linkage 1250, a second driven linkage 1270, and an output shaft 1236. The shaft 1202 may be operatively connected to a motor such that the shaft 1202 is driven by the motor. The first driver linkage 1240 and the second driver linkage 1250 may be connected to the shaft 1202 such that the first driver linkage 1240 and the second driver linkage 1250 are capable of rotating with respect to the shaft 1202.

The first driver linkage 1240 may be pivotally connected to the first driven linkage 1260 via pin 1238, in some embodiments. Similarly, the second driver linkage 1250 may be pivotally connected to the second driven linkage 1270 via a pin, in some embodiments.

The first driven linkage 1260 comprises at least one engagement element 1262 which is capable of intermeshing with a first receiving element 1264. As shown, the engagement element 1262 may comprise a tooth, and the receiving element 1264 may comprise a recessed area for receiving the tooth of the engagement element 1262. The receiving element 1264 may be fixed to the output shaft 1236 such that rotational motion imparted to the receiving element 1264 may thereby be transferred to the output shaft 1236.

Similarly, the second driven linkage 1270 may comprise at least one engagement element 1272 which is capable of intermeshing with a second receiving element 1274. The at least one engagement element 1272 of the second driven linkage 1270 and the second receiving element 1274 may be configured as described above with regard to the engagement element 1262 and receiving element 1264. The second receiving element 1274 may be fixed to the output shaft 1236 such that rotational motion imparted to the second receiving element 1274 may be transferred to the output shaft 1236.

The first driver linkage 1240 and the first driven linkage 1260 may have different lengths in order to impart a particular angular displacement to the output shaft 1236. In some embodiments, the first driver linkage 1240 and the first driven linkage 1260 may have equal lengths. The second driver linkage 1250 and the second driven linkage 1270 may be similarly configured. The analysis of the relative lengths of the linkages to achieve a particular displacement is founded on principles which are generally well known, e.g. four bar linkage analysis.

As shown in FIG. 12A, when the first engagement element 1262 is engaged with the first receiving element 1264, the output shaft 1236 may have a first angular displacement. The first angular displacement may be similar to the angular displacement described heretofore. In this configuration, the second engagement element 1272 may be disengaged with the second receiving element 1274.

As shown in FIG. 12B, when the second engagement element 1272 is engaged with the second receiving element 1274, the output shaft 1236 may have a second angular displacement. The second angular displacement may be similar to the angular displacement described heretofore. However, the first angular displacement may be different from the second angular displacement. For example, the first angular displacement may be greater than the second angular displacement. As another example, the first angular displacement may be less than the second angular displacement.

Figure 5:
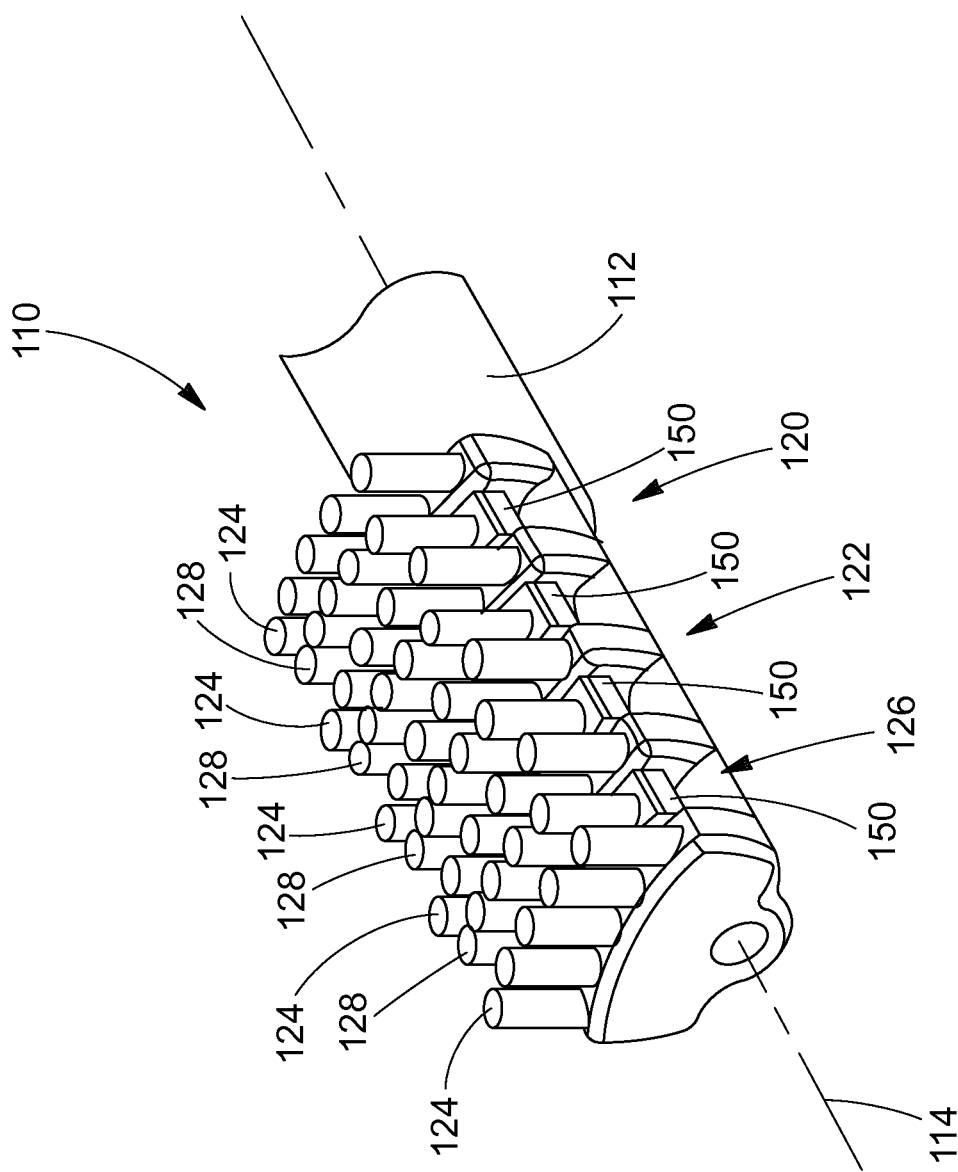
FIG. 5 is a schematic partial perspective view of another brush section.
Figure 6:
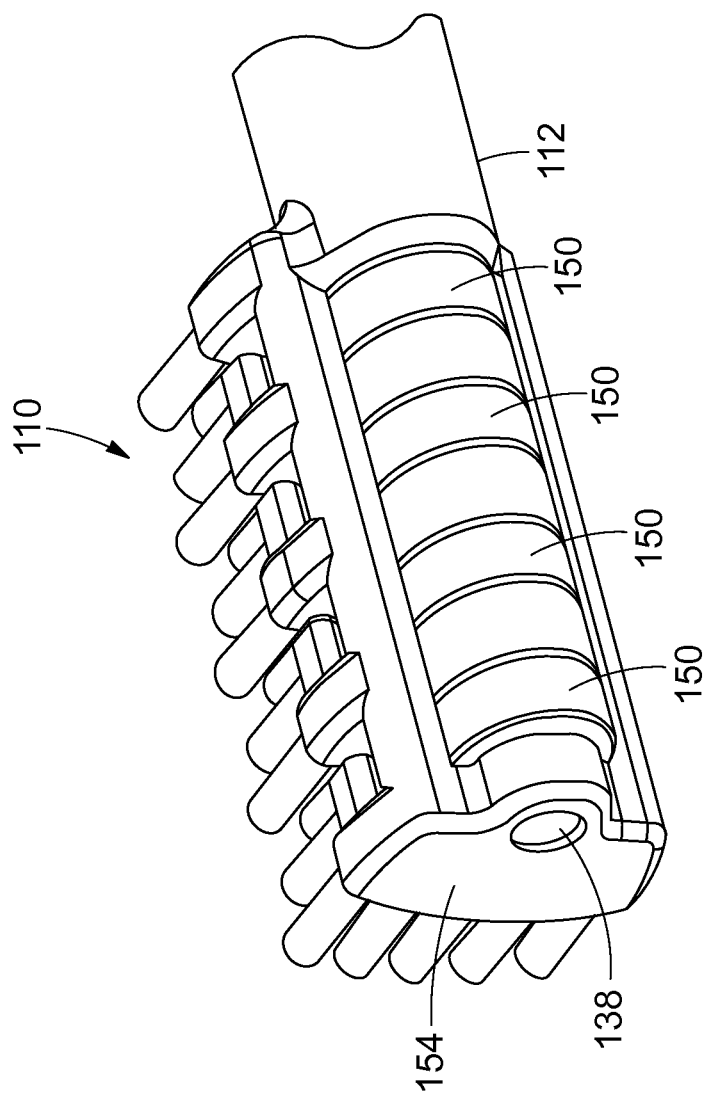
FIG. 6 is a schematic partial (bottom) perspective view of a brush head portion of the brush section illustrated in FIG. 5.

Referring to FIGS. 5-6 another embodiment of a brush section 110 is shown. Like elements of the brush section 110 to those of the brush section 10 are indicated using a reference numeral incremented by 100. The brush section 110 includes a mounting tube 112 extending along an axis 114. At a first end (not depicted), the mounting tube 112 is adapted to be push-fitted onto a handle section in a manner preventing relative rotation, as discussed previously with regard to the mounting tube 12.

At a second end 120 the brush section 110 includes a brush head portion 122. The brush head portion 122 supports a first plurality of contact elements 124 that are mounted to the head portion 122 so as to be fixed, i.e., static relative to the head portion 122. Any suitable method of mounting the first plurality of contact elements 124 to the head portion 122 may be used, such as those methods discussed heretofore with regard to the first plurality of contact elements 24. Supported within the head portion 122 is a movable contact element support or movable contact element holder 126 supporting a second plurality of contact elements 128. The second plurality of contact elements 128 may be mounted to the movable contact element holder 126 using any suitable method, such as those discussed heretofore with regard to the second plurality of contact elements 28. The movable contact element holder 126 may be supported within the head portion 122 such that the movable contact element holder 126 is able to rotate about the axis 114 responsive to a suitable driving input from a handle section.

The first plurality of contact elements 124 may have a first height and the second plurality of contact elements 128 may have a second height, different than the first height. Additionally, the ends of the first and second pluralities of contact elements 124 and 128 may have contoured, rounded or otherwise shaped ends. Among the first plurality of contact elements 124 and the second plurality of contact elements 128, contact elements at different locations of the head portion 122 front to back and center to edge may also have different heights and different end contours. The first plurality of contact elements 124 may be arranged in rows transverse relative to the axis 114. Similarly, the second plurality of contact elements 128 may be arranged in rows transverse relative to the axis 114.

As shown in FIG. 6, the movable contact elements holder 126 may include a plurality of separately movable contact element holder portions 150, each supporting a portion of the second plurality of contact elements 128. For example, each contact element holder portion 150 may support a separate transverse row of the second plurality of contact elements 128. The drive shaft 138 may extend through the head portion 122 and may be rotatably supported in an end member 154. The drive shaft 138 can be adapted to engage a drive member of a handle portion to which the brush section 110 is configured to operatively couple. Each movable contact element holder portion 150 may couple to the drive shaft 138 such that oscillation of the drive shaft 138 causes a like oscillation of the respective contact element portion 150. Each contact element holder portion 150 may be snap-fitted into the head portion 122 via an aperture 142 (shown in FIG. 7) and engaged with the drive shaft 138. A housing member (not depicted) may be provided to enclose the aperture 142. Additionally, the contact element holder portions 150 may be snap-fitted from a front side of the head portion 122.

As noted, each contact element holder portion 150 may be linked directly to the drive shaft 138 and thus to have an oscillating angular cleaning motion. Alternatively, at least some of the contact element holder portions 150 may be coupled by a linkage, cam structure or the like such that the contact element holder portion 150 has a cleaning motion separate from a rotating motion of the drive shaft 138 and/or a separate cleaning motion from other contact element holder portions 150.

Figure 7:
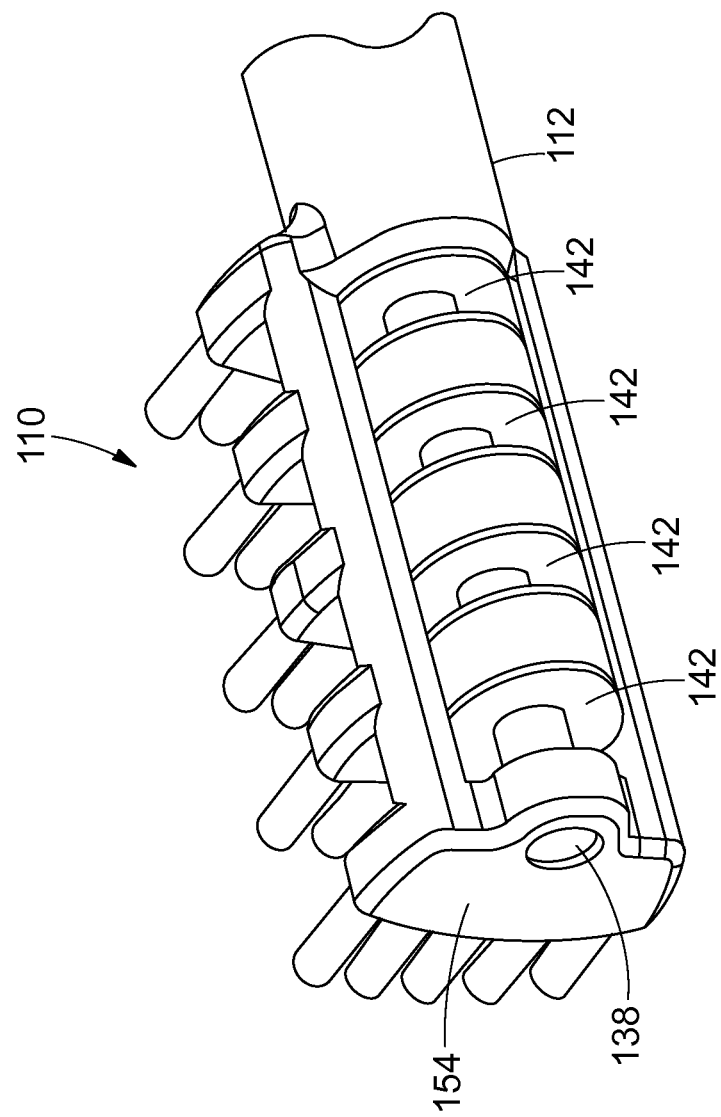
FIG. 7 is a schematic partial (bottom) perspective view of the brush head portion of FIG. 6 with the contact element holder portions removed for visual facilitation.

In the embodiment shown in FIGS. 5-7, each of the second plurality of contact elements 128 may be driven to oscillate back and forth angularly about the axis 114 to provide a cleaning action simulating an up-down manual brushing action. The second plurality of contact elements 128 may move through an angle of about 44 degrees, +/−22 degrees relative to the head portion 122. However, other angles greater than 44 degrees or less than 44 degrees may be used. In the embodiments described in FIGS. 5-7, any suitable angle may be utilized similar to those disclosed heretofore with regard to FIGS. 1-4.

In a similarly advantageous manner, the cleaning movement of the second plurality of contact elements 128 and a manually imparted cleaning movement of the head portion 122 by the user may provide an enhanced and effective cleaning action without drawing away from or degrading the driven cleaning action. The brush section 110 is also easily used in the same manner as a manual toothbrush to affect cleaning.

It is noted with respect to the brush section 110 that at least some of the contact element holder portions 150 may be separately coupled to the drive shaft 138 via a linkage, cam or similar structure to have a cleaning motion separate from an oscillating motion of the drive shaft 138. For example, as shown in FIG. 8, the drive shaft 138 may comprise a plurality of cams 160 offset from or eccentric relative to the axis 114. In some embodiments, each bristle holder portion 150 may be rotatably supported by engagement of a circular aperture 162 with a pin 166 formed on a static bristle support 164, a plurality of which, potentially corresponding to the number of rows of the first plurality of bristles 124, may be formed on the head section 122. Each cam 160 may engage a slot 168 formed in the bristle support portion 150 such that rotation of the drive shaft 138 causes a back and forth angular rotation of the bristle support portion 150 and the associated second plurality of bristles 128. Arrangement of the cams 160 on the drive pin 138 permits each bristle holder portion 150 to have a separate rotating motion, which may enhance the cleaning action of the head section 122.

Advantageously, a complex drive motion of the drive shaft 138 may be avoided, as it may be driven in rotation with the action of the cam 160 engaging the bristle support portion 150 to provide the desired cleaning motion for the second plurality of bristles 128. For example, some embodiments may utilize a drive shaft which oscillates back and forth about the axis 114 to achieve the oscillatory motion of the first plurality of contact elements, the second plurality of contact elements, and/or the third plurality of contact elements. As yet another example, some embodiments, may utilize a drive shaft which rotates about the axis 114 to achieve the oscillatory motion of the first plurality of contact elements, the second plurality of contact elements, and/or the third plurality of contact elements.

As shown in FIG. 9, an alternate arrangement of the bristle holder portions 150, designated as bristle holder portions 150' is contemplated. As shown, each bristle holder portion 150' may be rotatably supported on the pin 166. However, instead of being formed with a circular aperture 162 (shown in FIG. 8), the bristle holder portion 150' may be formed with a slot 162' which engages the pin 166. Additionally, the slot 168 (shown in FIG. 8) may be formed as a circular opening 168' within which the cam 160 rotates with rotation of the drive shaft 138. Rotation of the drive shaft 138 causes a back and forth angular rotation of the bristle support portion 150' and the associated second plurality of bristles 128. Additionally, the bristle support portions 150' may be driven linearly along the slot 162' relative to the axis 114. This arrangement of bristle support portions 150' permits each bristle holder portion 150' to have a rotating and translating motion, which may enhance the cleaning action of the head section 122. Also, arrangement of the cams 160 on the drive shaft 138 may allow each individual bristle holder portion 150' to have a motion separate and distinct from each other bristle holder portion 150'. The resulting relatively complex cleaning motion may be imparted to the second plurality of bristles 128 without a complex drive motion of the drive shaft 138, which may be driven in rotation.

Figure 10:
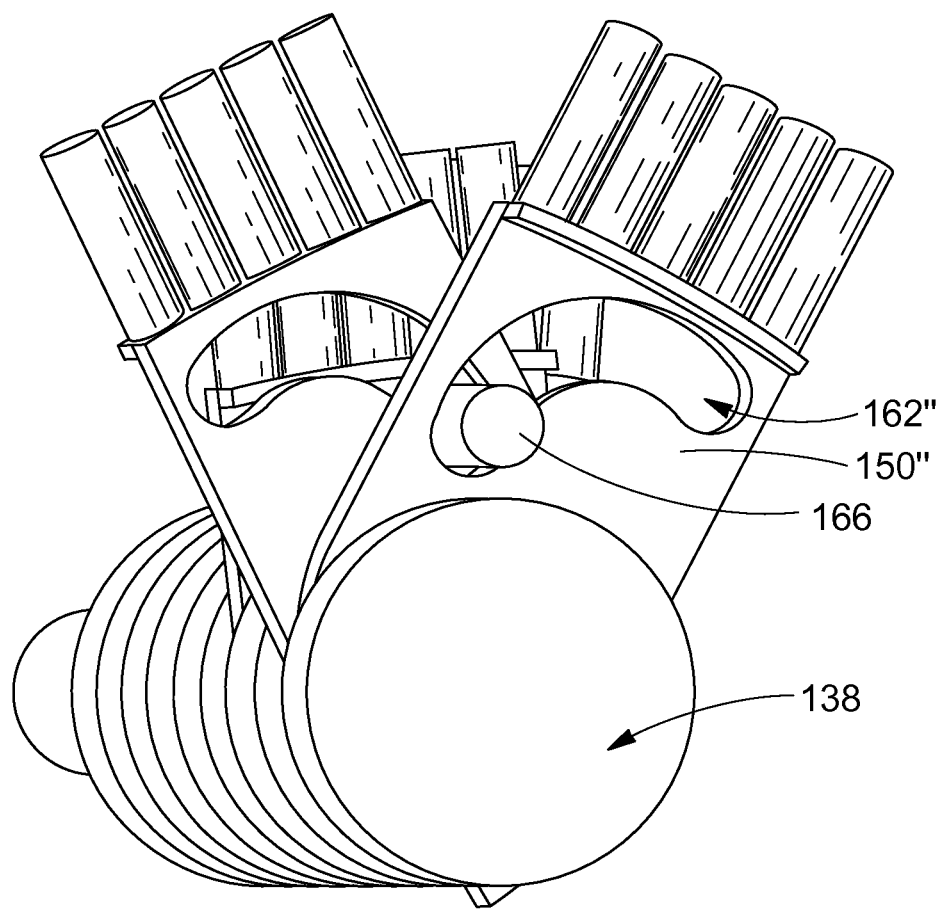
FIG. 10 is a schematic partial perspective view of a still further alternative brush head portion arrangement.

FIG. 10 illustrates yet another alternate arrangement of the bristle holder portions 150, designated as bristle holder portions 150". Each bristle holder portion 150" may be formed with an arcuate slot 162" that engages a corresponding pin 166 formed on a static bristle support. The drive shaft 138 may include eccentric cams such that rotation of the drive shaft 138 may provide rotating and translating motion of the bristle holder portions 150" via engagement of the drive shaft 138 with the respective bristle holder portions 150". Additionally, this arrangement may provide separate and distinct rotational and translation motion for each bristle holder portion 150" without a complex drive motion of the drive shaft 138.

As described, the various arrangements of a bristle holder portion, e.g., 150, 150' and 150", etc., permit relatively complex rotational and translational cleaning motions to be imparted to the second plurality of bristles 128. This may be accomplished with a simple rotating motion of the drive shaft 138 making brush sections 110 incorporating these configurations easily adaptable to existing handle section designs that may provide only for a rotating drive shaft output.

The first plurality of contact elements 24, the second plurality of contact elements 28, and/or the third plurality of contact elements 46 of the present invention may comprise a wide variety of materials and may have a number of different configurations. Any suitable material and/or any suitable configuration may be utilized.

For example, in some embodiments, the first plurality of contact elements 24, the second plurality of contact elements 28, and/or the third plurality of contact elements 46, may comprise tufts. The tufts may comprise a plurality of individual filaments which are securely attached to a cleaning element carrier. Such filaments may be polymeric and may include polyamide or polyester. The longitudinal and cross sectional dimensions of the filaments of the invention and the profile of the filament ends can vary. Additionally, the stiffness, resiliency and shape of the filament end can vary. Some examples of suitable dimensions include a length between about 3 cm to about 6 cm, or any individual number within the range. Additionally, the filaments may include a substantially uniform cross-sectional dimension of between about 100 to about 350 microns, or any individual number within the range. The tips of the filaments may be any suitable shape, examples of which include a smooth tip, a rounded tip, and a pointed tip. In some embodiments, the filaments may include a dye which indicates wear of the filaments as described in U.S. Pat. No. 4,802,255. Other suitable examples of filaments are described in U.S. Pat. No. 6,018,840. In some embodiments, the cleaning element fields may comprise fins as described in U.S. Pat. No. 6,553,604, and U.S. Patent Application Publication Nos. 2004/0177462; 2005/0235439; and 2005/0060822. In some embodiments, the cleaning element fields may comprise a combination of fins and tufts.

Additionally, at least a portion of some of the first plurality of contact elements 24, the second plurality of contact elements 28, and/or the third plurality of contact elements 46 may be attached to a cleaning element carrier at an angle. Such orientations are described in U.S. Pat. No. 6,308,367. Also, any suitable method may be utilized to attach the first plurality of contact elements 24, the second plurality of contact elements 26, and/or the third plurality of contact elements 46 to their respective structures.

Embodiments are contemplated where the mounting tube 12, 112 (shown in FIGS. 1-3 and 5-9) respectively, is angled with respect to the handle section. In such embodiments, the drive shaft of the present invention may be provided in discrete portions thereby accommodating the angle of the mounting tube 12, 112. For example, the drive shaft may include one or more universal joints. As yet another example, the drive shaft may be constructed from a compliant material. Some examples of suitable materials for construction of the drive shaft include aluminum, spring steel, plastics, e.g. delrin, nylon, polypropylene, and/or combinations thereof.

Referring to FIGS. 13A-13E another embodiment of a brush section 210 is shown. Like elements of the brush section 210 to those of the brush section 10 are indicated using a reference numeral incremented by 200. The brush section 210 includes a mounting tube 212 extending along an axis 214. At a first end 216, the mounting tube 212 is adapted to be push-fitted onto a handle section in a manner preventing relative rotation, as discussed previously with regard to the mounting tube 12.

At a second end 220 the brush section 210 includes a brush head portion 222. The brush head portion 222 supports a first plurality of contact elements 224 that are mounted to the head portion 222 so as to be fixed, i.e., static relative to the head portion 222. Any suitable method of mounting the first plurality of contact elements 224 to the head portion 222 may be used, such as those methods discussed heretofore with regard to the first plurality of contact elements 24. Supported within the head portion 222 is a movable contact element support or movable contact element holder 226 supporting a second plurality of contact elements 228. The second plurality of contact elements 228 may be mounted to the movable contact element holder 226 using any suitable method, such as those discussed heretofore with regard to the second plurality of contact elements 28. The movable contact element holder 226 may be supported within the head portion 222 such that the movable contact element holder 226 is able to rotate about the axis 214 responsive to a suitable driving input from a handle section. The second plurality of contact elements 228 extend through apertures 270 formed in the head portion 222 so that the contact elements 224 and 228 form a unitary contact element field to perform a brushing operation. In operation, the second plurality of contact elements 228 move with respect to the first plurality of contact elements 224, in a motion very similar to the motion a user would perform with a manual oral cleaning device such as a manual toothbrush.

The first plurality of contact elements 224 may have a first height and the second plurality of contact elements 228 may have a second height, different than the first height. Additionally, the ends of the first and second pluralities of contact elements 224 and 228 may have contoured, rounded or otherwise shaped ends. Among the first plurality of contact elements 224 and the second plurality of contact elements 228, contact elements at different locations of the head portion 222 front to back and center to edge may also have different heights and different end contours. The first plurality of contact elements 224 may be arranged in rows transverse relative to the axis 214. Similarly, the second plurality of contact elements 228 may be arranged in rows transverse relative to the axis 214. The rows of the first plurality of contact elements 224 may advantageously be longer in length than the rows of the second plurality of contact elements 228.

As shown in FIGS. 13A to 13E, the movable contact element holder 226 may be a single, unitary member supporting the second plurality of contact elements 228. The drive shaft 238 (not shown) may extend through the head portion 222 and is supported in an extension portion 244 of the movable contact element holder 226. The drive shaft 238 can be adapted to engage a drive member of a handle portion to which the brush section 210 is configured to operatively couple. The movable contact element holder 226 is coupled to the drive shaft 238 such that oscillation of the drive shaft 238 causes a like oscillation of the movable contact element holder 226. Alternatively, the movable contact element holder 226 may be coupled by a linkage, cam structure or the like such that the movable contact element holder 226 has a cleaning motion separate from a rotating motion of the drive shaft 238. The movable contact element holder 226 may be snap-fitted into the head portion 222 and engaged with the drive shaft 238.

In the embodiment shown of FIGS. 13A to 13E, each of the second plurality of contact elements 228 may be driven to oscillate back and forth angularly about the axis 214 to provide a cleaning action simulating an up-down manual brushing action. The second plurality of contact elements 228 may move through an angle of about 44 degrees, +/−22 degrees, relative to the head portion 222 in a free or unloaded condition when the brush section 210 is not in use. However, other angles greater than 44 degrees or less than 44 degrees may be used. In the embodiments described in FIGS. 13A to 13E, any suitable angle and oscillation frequency may be utilized similar to those disclosed heretofore.

In a similarly advantageous manner, the cleaning movement of the second plurality of contact elements 228 and a manually imparted cleaning movement of the head portion 222 by the user may provide an enhanced and effective cleaning action without drawing away from or degrading the driven cleaning action. The brush section 210 is also easily used in the same manner as a manual toothbrush to affect cleaning.

In the embodiment shown in FIGS. 13A to 13E, the movable contact element holder 226 includes an integral extension portion 244 supporting a third plurality of contact elements 246. Any suitable method of mounting the third plurality of contact elements 246 to the extension portion 244 may be used, such as those methods discussed heretofore. Other embodiments may include a similar extension portion (not shown) having a different freedom of motion relative to the head portion 222 and relative to the movable contact element holder 226. In the illustrated embodiment, the third plurality of contact elements 246 extend in a direction which is somewhat angled with respect to the upper side of the head portion 222, whereas the first and second pluralities of contact elements 224 and 228 are substantially perpendicular to the upper side of the head portion 222.

Figure 13C:
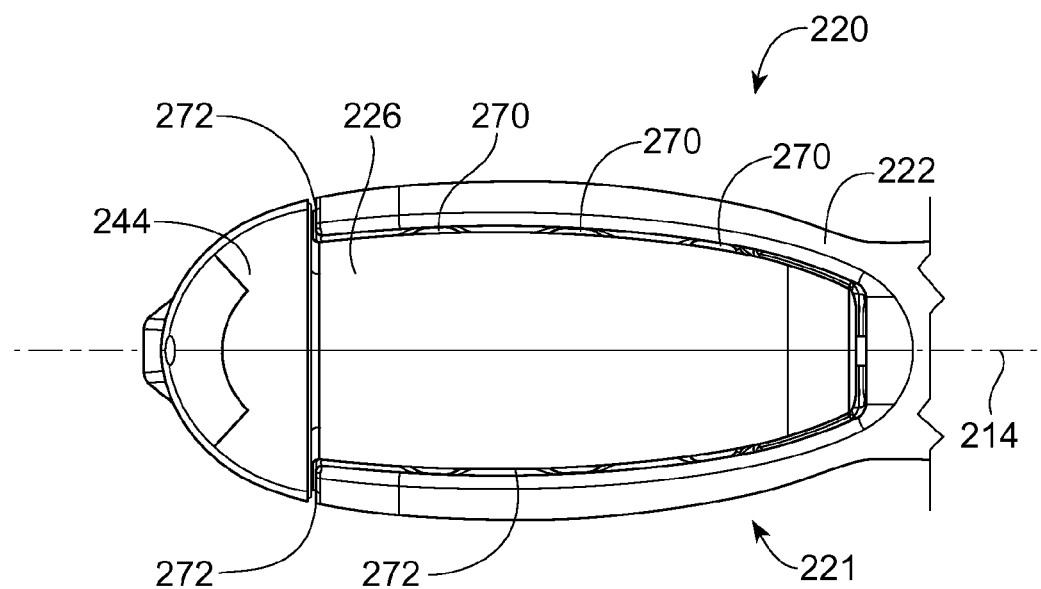
FIG. 13C is a back view of the head portion of the brush section illustrated in FIGS. 13A and 13B.
Figure 13D:
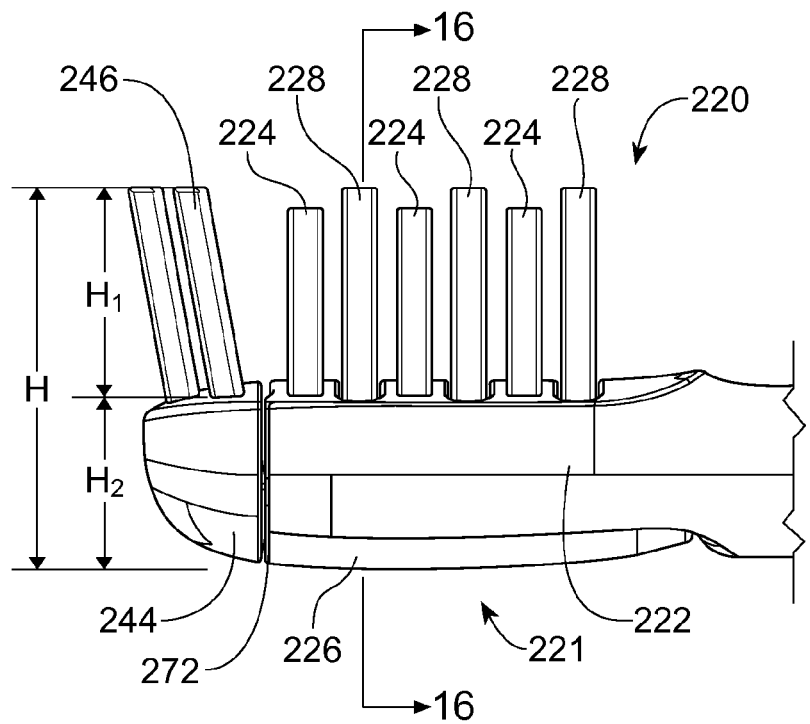
FIG. 13D is a side view of the head portion of the brush section illustrated in FIGS. 13A to 13C.

As illustrated for example in FIG. 13C, there is a gap 272 between the movable contact element holder 226 and the head portion 222. In the particular embodiment of FIG. 13C, the gap 272 includes a substantially U-shaped portion on the back side 221 of the head portion 222. As indicated in FIGS. 13B, 13C and 13D, that gap 272 further extends around the periphery of the head portion 222, between the head portion 222 and the extension portion 244 of the movable contact element holder 226. As the movable contact element holder 226 rotates about the longitudinal axis 214, there will be relative movement between the holder 226 and the head portion 222. To avoid the potential risk of injury caused by that relative motion pinching the mucosa, the width of the gap 272 should be minimized. A minimal width gap 272 is also advantageous because it reduces the size of the brush head. At the same time, the gap 272 preferably remains wide enough so that water, saliva, toothpaste, or other materials present in the mouth during a tooth brushing operation can easily pass through the gap 272. In that way, the toothbrush may more effectively be cleaned when the tooth brushing operation is compete by rinsing the brush section with water, which passes through the apertures 270 and then through the gap 272.

In some embodiments, the width of the gap 272 at a particular point within the head portion 222 may change as the movable contact element holder 226 moves through its rotation cycle. In other embodiments, the width of the gap 272 may remain substantially constant during such movement, which advantageously helps to prevent a "suctioning" of the mucosa into the gap 272. The width of the gap 272 may be different at different points within the head portion 222, or the gap 272 width may be substantially the same along the entire extent of the gap 272.

In some embodiments, for example, the width of the gap 272 between the movable contact element holder 226 and the head portion 222 remains within a range of between about 0.1 mm and about 0.6 mm throughout the rotation cycle. In some embodiments, the width of the gap 272 throughout the rotation cycle can be at least 0.1 mm, at least 0.15 mm, at least 0.2 mm, at least 0.25 mm, at least 0.3 mm, at least 0.35 mm, at least 0.4 mm, at least 0.45 mm, at least 0.5 mm, at least 0.55 mm, and/or at most 0.6 mm, at most 0.55 mm, at most 0.5 mm, at most 0.45 mm, at most 0.4 mm, at most 0.35 mm, at most 0.3 mm, at most 0.25 mm, at most 0.2 mm, or at most 0.15 mm.

Figure 14A:
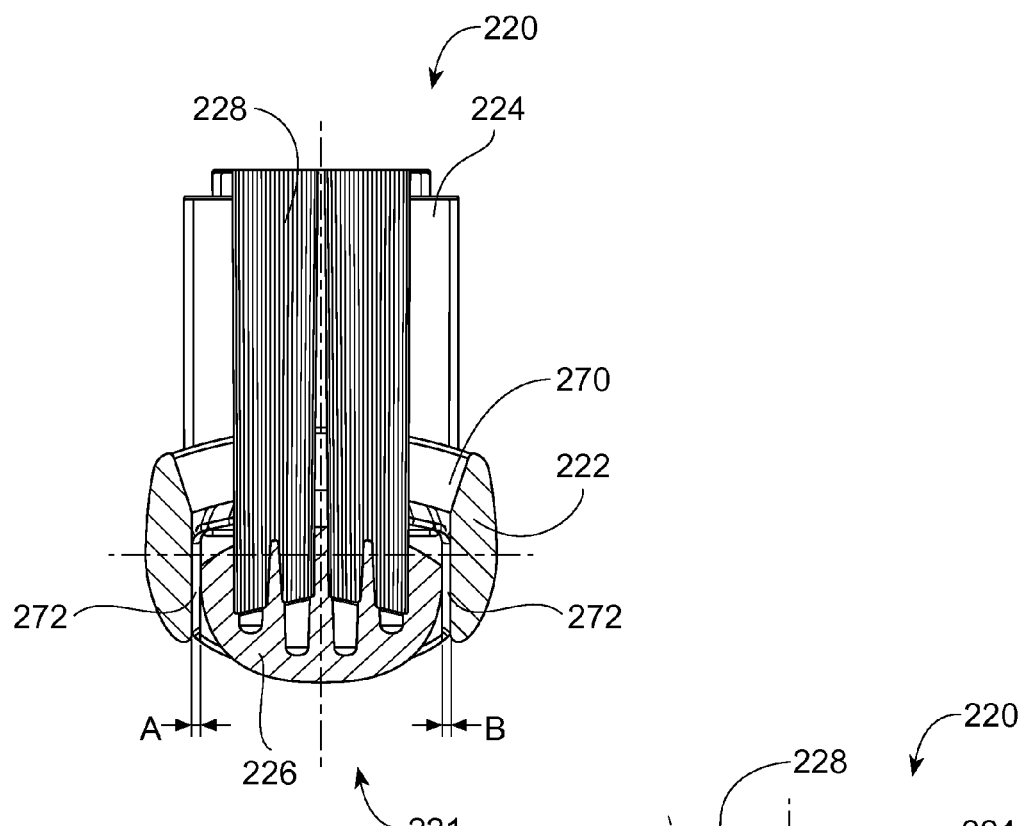
FIGS. 14A and 14B are transverse cross-sectional views taken through line 14-14 in FIG. 13C.
Figure 14B:
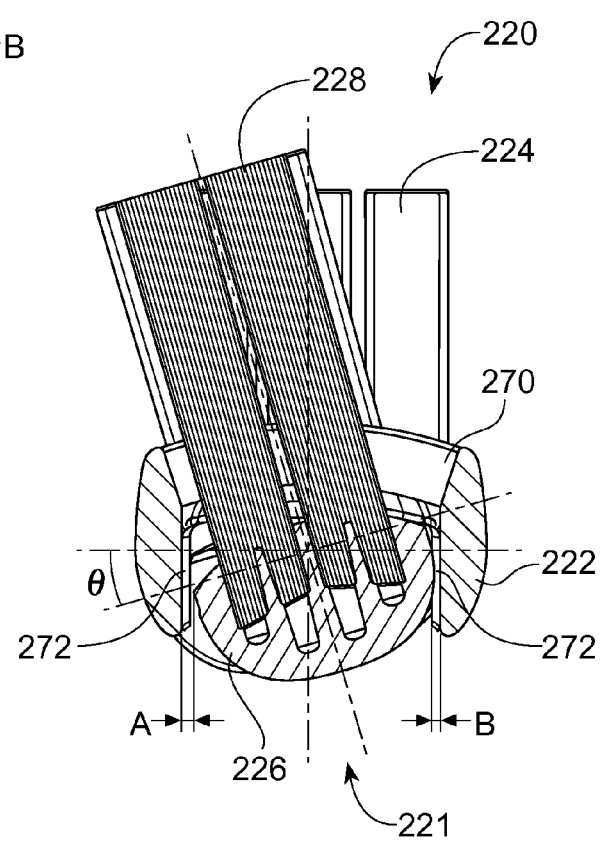

FIGS. 14A and 14B illustrate the rotation cycle of the movable contact element holder 226 within the head portion 222. FIG. 14A shows the holder 226 in its neutral state, where the +/− angle θ is zero degrees. FIG. 14B shows the holder 226 at its maximally deflected state to one side (to the left as oriented in this illustration) in a loaded, in-use condition, where the rotary movement switches from a counter-clockwise rotation to a clockwise rotation. As can be seen the width of the gap 272 at points A and B changes through the course of the oscillation. In some embodiments, the width of the gap 272 at point A is about 0.27 mm in the neutral state and about 0.45 mm in the maximally deflected state, and the width of the gap at point B is about 0.27 mm in the neutral state and about 0.22 mm in the maximally deflected state. In an alternative embodiment not shown in the figures, the width of the gap 272 at points A and B may be maintained substantially constant through the rotation cycle if the radius of curvature of the outer surface of the movable contact element holder 226 is appropriately configured, as will be appreciated by one of ordinary skill in the art. For example, the radius of curvature in the region of the gap 272 may be substantially constant.

Additional measures may be employed to help prevent pinching of the mucosa between the movable contact element holder 226 and the head portion 222. For example, the interface between the holder 226 and the head portion 222 across the gap 272 or portions of the gap 272 may be substantially continuous, lacking sharp discontinuities during the rotation cycle. As illustrated in FIGS. 13C and 13D, the interface between the holder 226 and the head portion 222 across the substantially U-shaped portion of the gap 272 on the back side 221 of the head portion 222 is substantially continuous during movement of the holder 226. This substantial continuity is also illustrated in FIGS. 14A and 14B. This particular embodiment may be advantageous because, during typical use of the brush section 210, the back side 221 will face and frequently contact the mucosa such as the interior cheek surface, the tongue, and the like.

Figure 13E:
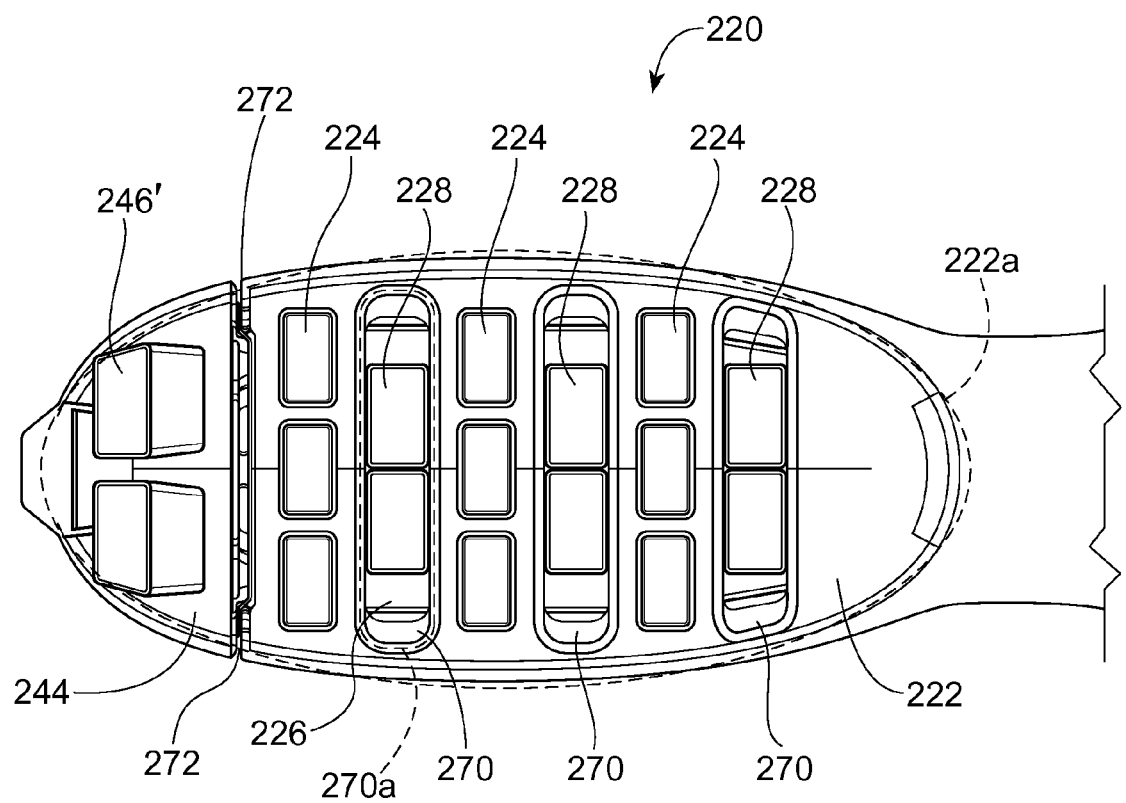
FIG. 13E is a top view of the head portion of the brush section illustrated in FIGS. 13A to 13D, and employing a different bristle configuration at the tip of the head.

Similarly, when the holder 226 is in its neutral state as shown for example in FIGS. 13B and 13E, the interface at the rest of the gap 272 (i.e. the portion between the extension portion 244 and the head portion 222) is also substantially continuous. When the holder 226 rotates away from that neutral position, however, the interface in that portion of the gap 272 will start to become discontinuous. As will be especially appreciated from FIG. 13B, the degree of discontinuity in the portion of the gap 272 between the extension portion 244 and the head portion 222 will increase as the holder 226 rotates further away from its neutral position. As one way to reduce this discontinuity, the angular extent of the rotation may be limited. As will be appreciated by one of ordinary skill in the art, this limitation of rotation may be accomplished in many ways, such as by appropriately configuring the coupling between the holder 226 and the electric drive in the handle, or by appropriately configuring the fit of the holder 226 into the head portion 222, or by other means.

For example, the rotation of the movable contact element holder 226 may be limited so that each of the second plurality of contact elements 228 remain within the vertical envelopes defined by the respective apertures 270 through which the elements 228 extend, such as shown by the dotted curve 270a in FIG. 13E. As an alternative example, the rotation of the movable contact element holder 226 may be limited so that each of the second plurality of contact elements 228 remain within the vertical envelope defined by the outer profile of the head portion 222, such as shown by the dotted curve 222a in FIG. 13E. In yet further embodiments, the rotation may be limited so that only a lower portion of the height $H_1$ of the contact elements 228 (see FIG. 13D) remains within one or the other of the envelopes 270a, 222a. The lower portion may be, for example, 75 percent, 50 percent, or 25 percent of the height $H_1$ of the contact elements 228.

Figure 15:
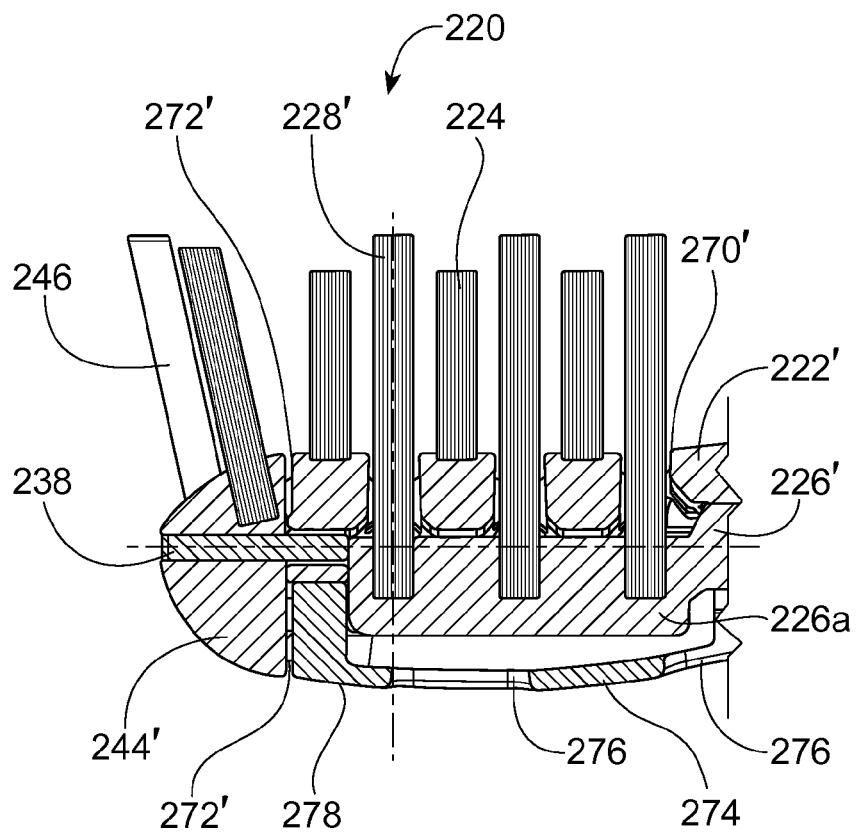
FIG. 15 is a cross-sectional view of another brush section head portion, including a cover portion.
Figure 16:
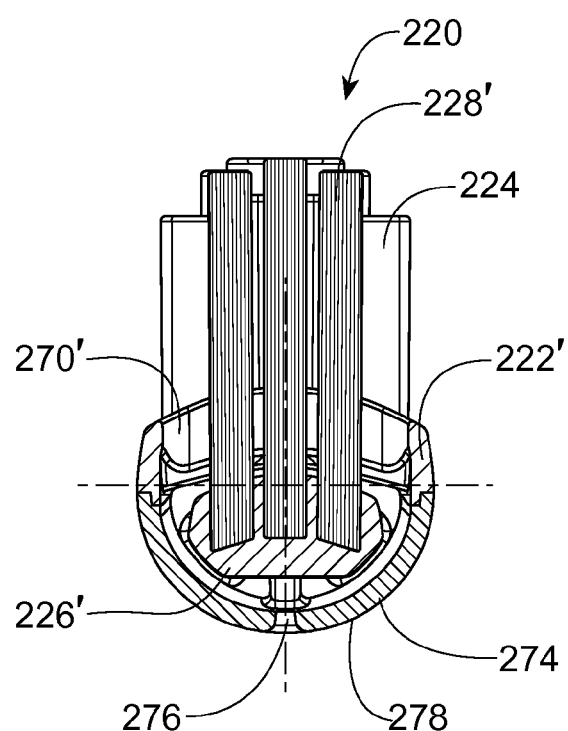
FIG. 16 is a transverse cross-sectional view taken through line 16-16 in FIG. 15.

In an alternate arrangement, shown for example in FIGS. 15 and 16, a cover member 274 may be utilized. The prime symbol is utilized in these figures to indicate elements which are similar and yet not identical to elements in FIGS. 13A to 13E. The attachment of the cover member 274 to the head portion 222' may be permanent or semi-permanent. Any method of attachment may be used such as a snap fit, ultrasonic bonding, or the like. The cover member 274 may be made of any suitable material such as a thermoplastic or even metal. Although not shown in the figures, the cover member may take the form of a thin, flexible skin covering which extends over one or more portions of the gap 272, made from for example a soft thermoplastic material. The thin, flexible skin can expand and contract or otherwise accommodate the movement of the holder 226 within the head portion 222, while at the same time covering the gap so that the mucosa will not be pinched between the holder 226 and the head portion 222 in the covered portion of the gap.

The cover member 274 as shown in FIGS. 15 and 16 operates to cover at least a portion of the movable contact element holder 226' and thereby prevent the mucosa from contacting the covered portion of the holder 226'. In the representative example of FIGS. 15 and 16, the covered portion is shown at 226a, while the extension portion 244' of the holder 226' is not covered by the cover member 274. Thus, the gap 272' between the extension portion 244' and the head portion 222' can be minimized to help prevent pinching of the mucosa at that interface, as already discussed above. The cover member 274 may include apertures such as shown at 276 in order to facilitate a rinsing operation to clean the brush section when a brushing operation is complete. Although not shown, the cover member 274 may include a transparent window portion so that the user of the brush can view the inner workings of the brush section, such as gearing and the like. In addition, the back surface 278 of the cover member 274 may be textured to provide a mucosa cleaning or massaging.

Figure 17:
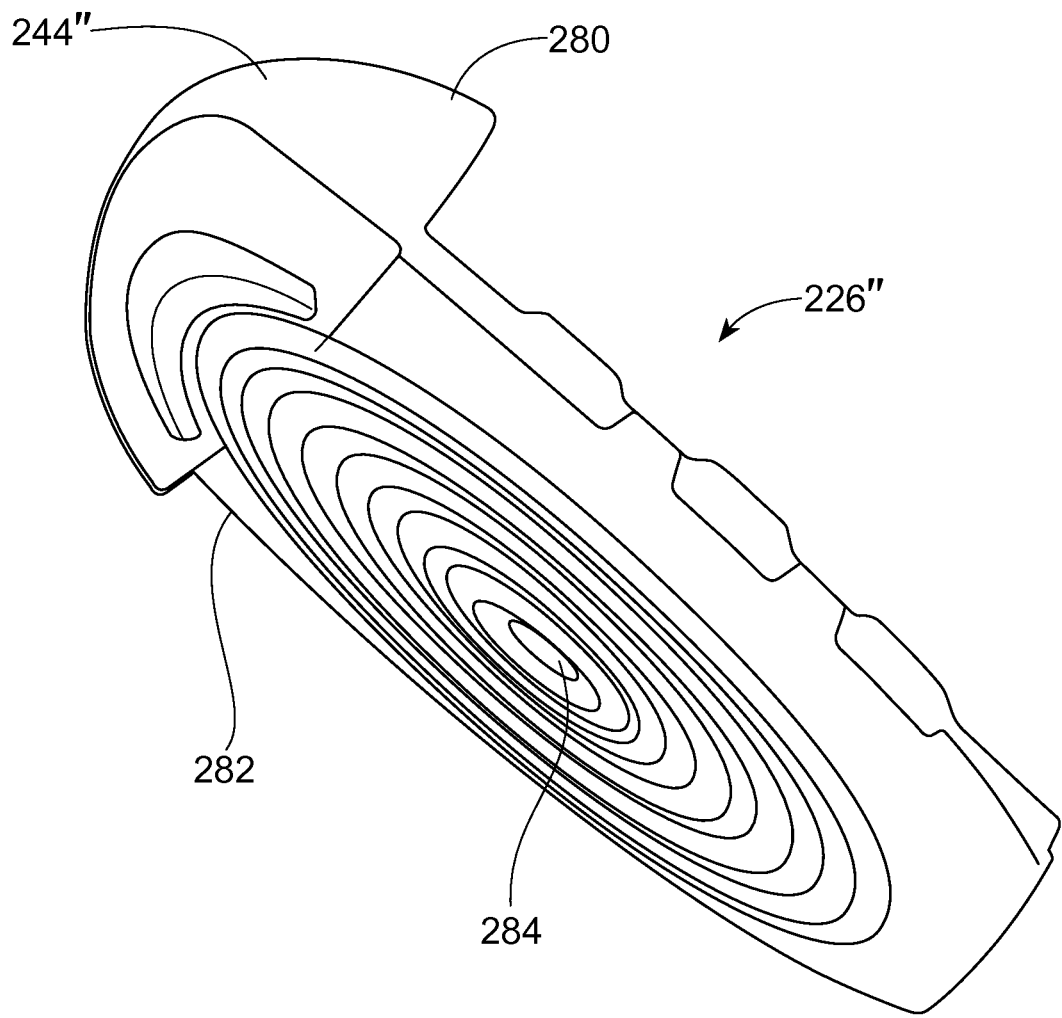
FIG. 17 is a perspective view of a movable contact element holder with a mucosa cleaning or massaging surface configuration.

The movable contact element holder may also include a mucosa cleaning or massaging surface, irrespective of whether a cover member 274 is present. This is shown, for example, in FIG. 17. The movable contact element holder 226" is manufactured from a first material 280 and a second material 282. The first material 280 is a relatively rigid material for structural stability. The second material 282 is a relatively soft material to provide a cleaning or massaging effect. As illustrated in FIG. 17, the second material 282 has a "water ripple" surface configuration 284 to enhance the cleaning or massaging effect. However, any such surface configuration may be used instead, such as straight ripples, knurls, ridges, ribs, bars, knobs, or any other such surface configuration known to one of ordinary skill in the art, and combinations thereof. Even a substantially smooth configuration surface may be used if the second material 282 itself provides a mucosa cleaning or massaging effect.

A further advantage of the present invention is a low profile brush head. In this context, a brush head's profile is the height H of the brush head as illustrated for example in FIG. 13D. In this regard, the height H in many instances is the combination of two separate components, the height $H_1$ of the longest contact elements in the toothbrush head and the height $H_2$ of the structure(s) which hold and support the contact elements. A low profile brush head may be desirable, for example, to reduce the overall size of the brush head and thus facilitate moving the brush around within the person's mouth, particularly to reach the rear molars and the inside tooth surfaces. A low profile brush head is thus particularly advantageous when used in a child's toothbrush.

A low profile brush head further more closely resembles a manual toothbrush. In many electric toothbrushes, $H_1$ is less than $H_2$, so that the ratio $H_1/H_2$ is less than 1. By contrast, in many manual toothbrushes, $H_1$ is greater than $H_2$ so that the ratio $H_1/H_2$ is more than 1. This difference between electric and manual toothbrushes is often easily discernable to consumers. So, in order to make an electric toothbrush look and feel more like a manual toothbrush to a consumer, it would be advantageous to have the ratio $H_1/H_2$ be equal to at least 1. This may most easily be accomplished by dispensing with a cover member, but it might also be achieved in conjunction with a cover member. To help reduce the height added by a cover member, the cover member may for example be made of metal or a thin, flexible skin.

Many different embodiments are described herein. One of ordinary skill will appreciate that any feature disclosed in connection with one embodiment may very well also work in connection with one or more other embodiments. As but one example of this interchangeability, the description of the gap between the movable contact element holder 226 and the head portion 222 of the brush section 210 may be applied to any other embodiment disclosed herein, such as the brush section 10 or the brush section 110.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The preceding text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be combined with or substituted for, in whole or part, any other feature, characteristic, component, composition, ingredient product, step or methodology described herein. Numerous alternative embodiments could be implemented, using either current technology or technology developed after the filing date of this patent, which would still fall within the scope of the claims.

What is claimed is:

1. A cleaning section for an electrical toothbrush, the cleaning section comprising:
   a head portion;
   a movable contact element holder supported within the head portion and structured to receive a drive motion from a motor via a drive mechanism comprising a drive shaft having a longitudinal axis, the drive shaft being structured to translate a motion generated by the motor to the movable contact element holder; and
   movable contact elements mounted to the movable contact element holder;
   wherein a gap is disposed between the head portion and the movable contact element holder, wherein a width of the gap remains between about 0.1 millimeter and about 0.6 millimeter throughout a full range of motion of the movable contact element holder.

2. The cleaning section of claim 1, further comprising static contact elements supported within the head portion, such that when the movable contact element holder moves, the movable contact elements move relative to the static contact elements.

3. The cleaning section of claim 2, wherein the movable contact elements and the static contact elements together define a height of a contact element field; and
   the head portion, the movable contact element holder, or both the head portion and the movable contact element holder define a support height underneath the contact element field; and
   wherein the contact element field height is larger than the support height.

4. The cleaning section of claim 1, wherein at least a portion of the gap is exposed to an exterior of the cleaning section.

5. The cleaning section of claim 1, wherein the movable contact element holder is disposed at least partly within the head portion, and the movable contact elements extend up through apertures in the head portion.

6. The cleaning section of claim 5, wherein the movable contact elements are arranged in one or more rows oriented transversely to the longitudinal axis.

7. The cleaning section of claim 1, wherein the movable contact element holder comprises an end extension portion including a third plurality of contact elements which move along with the movable contact elements.

8. The cleaning section of claim 1, further comprising a cover member which covers at least part of the gap.

9. The cleaning section of claim 1, wherein the cleaning section comprises an end portion which may be detachably coupled to a handle portion of the electrical toothbrush.

10. The cleaning section of claim 1, wherein the width of the gap remains between about 0.1 millimeter and about 0.6 millimeter in a neutral state of the movable contact element support, and remains between about 0.2 millimeter and about 0.45 millimeter in a maximally deflected state of the movable contact element holder in a loaded, in-use condition.

11. The cleaning section of claim 1, wherein the width of the gap throughout at least a portion of the gap remains substantially constant during movement of movable contact element holder.

* * * * *